(12) United States Patent
Goldshleger et al.

(10) Patent No.: US 11,266,495 B2
(45) Date of Patent: Mar. 8, 2022

(54) LIGHT ADJUSTABLE INTRAOCULAR LENS WITH A MODULABLE ABSORPTION FRONT PROTECTION LAYER

(71) Applicant: RxSight, Inc., Aliso Viejo, CA (US)

(72) Inventors: Ilya Goldshleger, Ladera Ranch, CA (US); John Kondis, Irvine, CA (US); Ritu Shrestha, Huntington Beach, CA (US)

(73) Assignee: RxSight, Inc., Aliso Viejo, CA (US)

( * ) Notice: Subject to any disclaimer, the term of this patent is extended or adjusted under 35 U.S.C. 154(b) by 0 days.

(21) Appl. No.: 16/658,142

(22) Filed: Oct. 20, 2019

(65) Prior Publication Data

US 2021/0113328 A1 Apr. 22, 2021

(51) Int. Cl.
*A61F 2/16* (2006.01)

(52) U.S. Cl.
CPC .......... *A61F 2/1624* (2013.01); *A61F 2/1627* (2013.01); *A61F 2/1635* (2013.01); *A61F 2/1659* (2013.01); *A61F 2002/1683* (2013.01); *A61F 2002/16965* (2015.04); *A61F 2210/0085* (2013.01); *A61F 2250/0001* (2013.01)

(58) Field of Classification Search
CPC .... A61F 2/1624; A61F 2/1627; A61F 2/1659; A61F 2002/16965
See application file for complete search history.

(56) References Cited

U.S. PATENT DOCUMENTS

| | | |
|---|---|---|
| 4,639,100 A | 1/1987 | Arnaud |
| 4,755,056 A | 7/1988 | Yasuda et al. |
| 5,229,797 A | 7/1993 | Futhey et al. |
| 5,258,024 A | 11/1993 | Chavel et al. |
| 5,432,876 A | 7/1995 | Appeldorn et al. |
| 5,549,668 A | 8/1996 | O'Donnell, Jr. |
| 5,638,212 A | 6/1997 | Meyers et al. |

(Continued)

FOREIGN PATENT DOCUMENTS

| | | |
|---|---|---|
| EP | 0331082 A1 | 9/1989 |
| JP | 2003-084242 A | 3/2003 |

(Continued)

OTHER PUBLICATIONS

Bethke, Walter, "An IOL You Can Customize," Review of Ophthalmology, (Sep. 2000).

(Continued)

*Primary Examiner* — Javier G Blanco
(74) *Attorney, Agent, or Firm* — Gergely T. Zimanyi

(57) ABSTRACT

Embodiments of a modulable absorption light adjustable lens (MALAL) comprise a light adjustable lens that is capable of changing its optical properties upon an adjusting irradiation, including a photo-modifiable material; and a modulable absorption front protection layer, including a modulable absorption compound whose absorption properties can be modulated with a modulating stimulus. Other embodiments include a method of adjusting an optical property of a modulable absorption light adjustable lens, the method comprising: reducing an absorption of a modulable absorption compound of a modulable absorption front protection layer of the MALAL by a modulating stimulus, the MALAL having been previously implanted into an eye; and changing an optical property of a light adjustable lens of the MALAL by applying an adjusting irradiation.

17 Claims, 19 Drawing Sheets

(56) References Cited

U.S. PATENT DOCUMENTS

| | | | |
|---|---|---|---|
| 5,684,636 | A | 11/1997 | Chow et al. |
| 5,777,719 | A | 7/1998 | Williams et al. |
| 5,998,096 | A | 12/1999 | Umemoto et al. |
| 6,086,204 | A | 7/2000 | Magnante |
| 6,139,147 | A | 10/2000 | Zhang |
| 6,325,792 | B1 | 12/2001 | Swinger et al. |
| 6,353,502 | B1 | 3/2002 | Marchant et al. |
| 6,382,795 | B1 | 5/2002 | Lai |
| 6,450,642 | B1 | 9/2002 | Jethmalani et al. |
| 6,476,983 | B2 | 11/2002 | Kodama et al. |
| 6,530,917 | B1 | 3/2003 | Seiler et al. |
| 6,575,572 | B2 | 6/2003 | Lai et al. |
| 6,604,098 | B1 | 8/2003 | Kung et al. |
| 6,648,473 | B2 | 11/2003 | Dellavecchia et al. |
| 6,824,266 | B2 | 11/2004 | Jethmalani et al. |
| 6,905,641 | B2 | 6/2005 | Platt et al. |
| 6,933,143 | B2 | 8/2005 | Sullivan et al. |
| 7,122,227 | B2 | 10/2006 | Vaughn-Spickers et al. |
| 7,892,711 | B2 | 2/2011 | Kondo et al. |
| 7,911,676 | B2 | 3/2011 | Knowles et al. |
| 7,955,665 | B2 | 6/2011 | Nishiyama et al. |
| 8,604,098 | B2 | 12/2013 | Boydston et al. |
| 8,933,143 | B2 | 1/2015 | Boydston et al. |
| 2003/0048411 | A1 | 3/2003 | Jethmalani et al. |
| 2005/0187622 | A1 | 8/2005 | Sandstedt et al. |
| 2006/0177605 | A1 | 8/2006 | Lub et al. |
| 2006/0193998 | A1 | 8/2006 | Harding et al. |
| 2007/0159594 | A9 | 7/2007 | Jani et al. |
| 2008/0094326 | A1 | 4/2008 | Yamaki et al. |
| 2008/0137030 | A1 | 6/2008 | Hoffman |
| 2008/0171143 | A1 | 7/2008 | Nishikawa et al. |
| 2008/0199782 | A1 | 8/2008 | Yoshizawa et al. |
| 2010/0052196 | A1 | 3/2010 | Yasuda et al. |
| 2011/0198546 | A1 | 8/2011 | Choi |
| 2011/0245919 | A1 | 10/2011 | Pettit |
| 2013/0222765 | A1 | 8/2013 | Thompson et al. |
| 2015/0217133 | A1 | 8/2015 | Angeley et al. |
| 2018/0338827 | A1 | 11/2018 | Goldshleger et al. |
| 2019/0227344 | A1 | 7/2019 | Bakaraju et al. |

FOREIGN PATENT DOCUMENTS

| | | |
|---|---|---|
| WO | 00/41650 A1 | 7/2000 |
| WO | 00/45759 A1 | 8/2000 |
| WO | 01/37031 A1 | 5/2001 |
| WO | 03/058287 A2 | 7/2003 |
| WO | 2006/003893 A1 | 1/2006 |
| WO | 2007/055316 A1 | 5/2007 |
| WO | 2012/006370 A2 | 1/2012 |

OTHER PUBLICATIONS

Brandser, Rennaug, et al., "Accuracy of IOL calculation in cataract surgery," Ophthalmological Journal of the Nordic Countries, vol. 75, No. 2., p. 162-165, (Apr. 1997).

Charters, Lynda, "New IOL lets laser adjust refraction postimplantation," Hotel & Motel Management, Opthamology Times, (Jul. 1, 2000).

Garcia-Amoros, Jaume, Kintetic study of the fast thermal cis-to-trans isomerization of para-, ortho- and , 2010,ys. Chem. Chem. Phys., 12, 13238-13242.

He, J. C., et al., "Measurement of the wave-front aberration of the eye by a fast psychophysical procedure," Optical Society of America, vol. 15, No. 9, p. 2449-2456, (Sep. 1998).

Henry, Ronald A., Aryl Diazomorpholides, 1943, Journal of American Chemical Society, vol. 65, pp. 479-480.

Ichinohe, 2003, JP 2003-084242 Machine Translation.

International Search Report issued for PCT/US01/30300, dated Mar. 13, 2002.

Liang, Junzhong, et al., "Aberrations and retinal image quality of the normal human eye," J. Opt. Soc. Am. A. Vol. 14, No. 11, p. 2873-2882, (Nov. 1997).

Liang, Junzhong, et al., ""Objective measurement of wave aberrations of the human eye with the use of a Hartmann-Shack wavefront sensor," Optical Society of America, vol. 11, No. 7, p. 1949-1957, (Jul. 1994).".

Lucke, K., et al., "A Method of lens extraction for the injection of liquid intraocular lenses," German Journal of Opthamology, 1992 vol. 1, No. 5., DD. 342-345.

Mahoney, Robert K., et al., "Laser Adjustable Lens: a new generation in implants," Ocular Surgery News, vol. 18, No. 15, (Aug. 1, 2000).

Oshika, Tetsuro, et al. "Three year prospective, randomized evaluation of intraolucar lens implantation through 3.2 and 5.5 mm incisions," J. Cataract Refract Surg, vol. 24, p. 509-514, (Apr. 1998).

Partial European Search Report issued for EP 01 97 5499, dated Apr. 11, 2005.

Roos, et al., Photonics Spectra, Circle 77 (2001).

Salmon, Thomas O., et al., "Comparison of the eye's wave-front aberration measured psychophysically and with the Shack-Hartmann wave-front sensor," Optical Society of America, vol. 15, No. 9, pp. 2457-2465, (Sep. 1998).

Liang, Junzhong, et al., "Supernormal vision and high-resolution retinal imaging through adaptive optics," Optical Society of America, vol. 14, No. 11, pp. 2884-2891, (Nov. 1997).

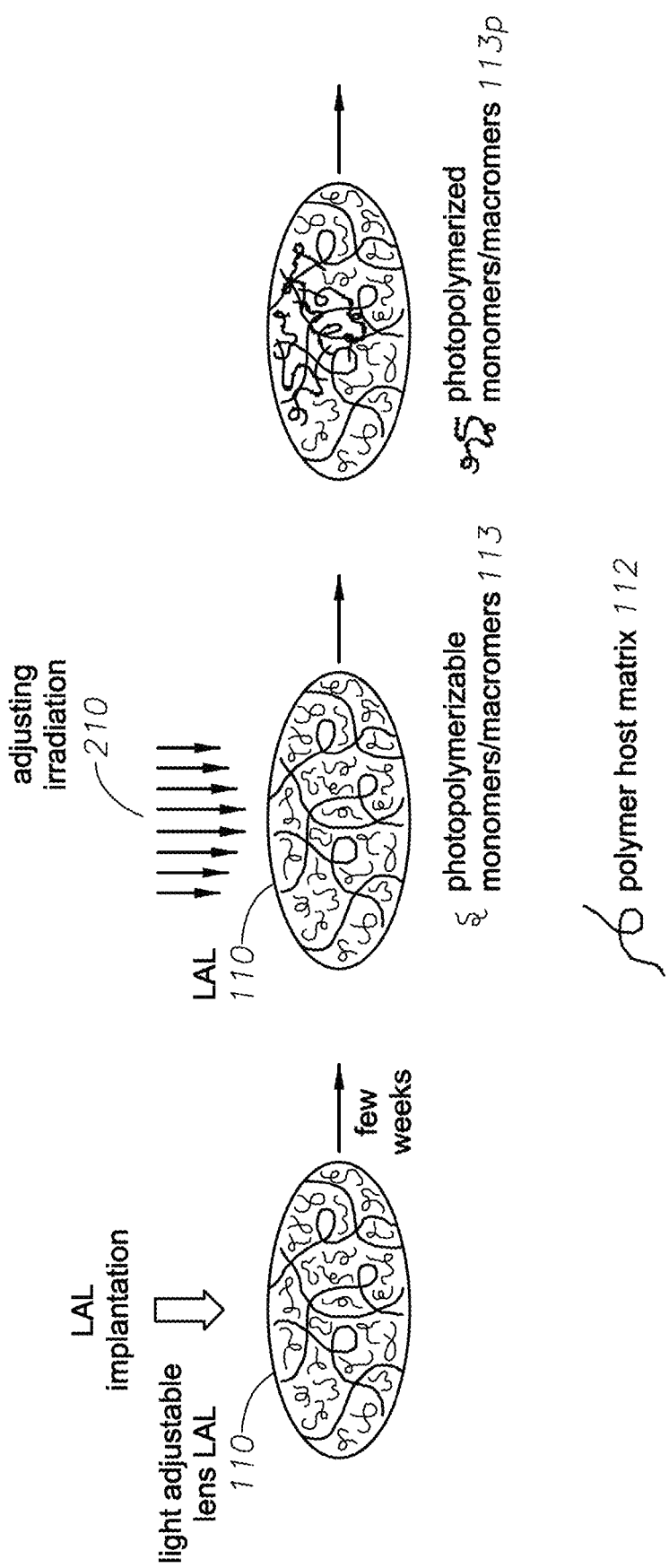

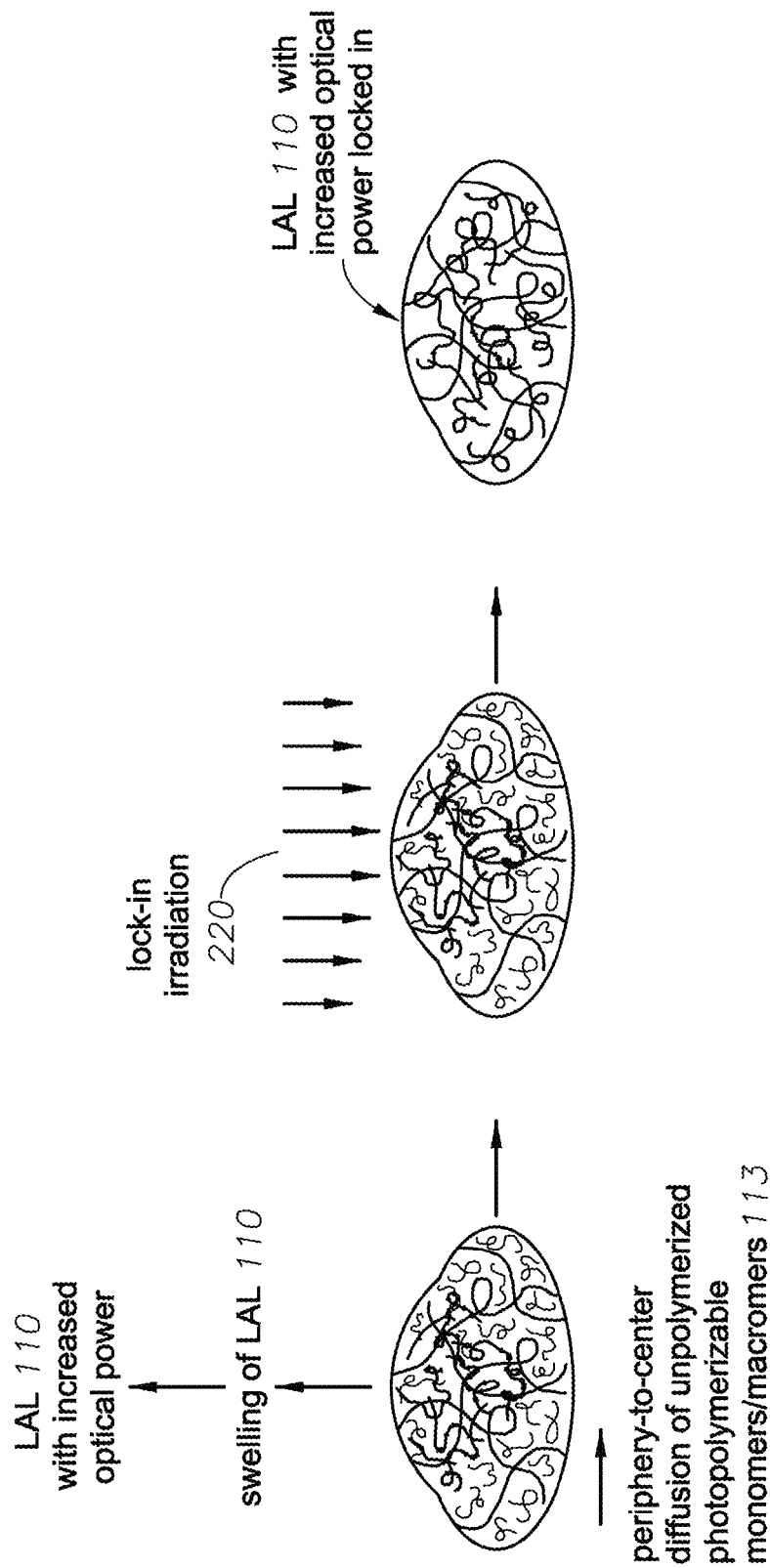

LIGHT ADJUSTABLE INTRAOCULAR LENS WITH A MODULABLE ABSORPTION FRONT PROTECTION LAYER

TECHNICAL FIELD

This invention relates to light adjustable lenses, and more specifically to light adjustable lenses with a modulable absorption.

BACKGROUND

The techniques and tools of cataract surgery are experiencing continuous, impressive progress. Subsequent generations of phacoemulsification platforms and newly invented surgical lasers keep increasing the precision of the placement of intraocular lenses (IOLs) and keep reducing the unwanted medical outcomes.

However, even if the IOLs are selected with careful planning and implanted with precision surgical equipment into the capsular bag, the post-implantation healing and scarring of the ophthalmic tissue often shifts or tilts the IOL away from its planned and optimal location in the capsular bag of the eye. This settling process can take a few weeks. This shift and tilt have the potential to worsen the optical performance of the IOL and thus the overall medical outcome of the cataract surgery.

Recently, an intraocular light adjustable lens (LAL) technology has been invented and developed to address this problem. Just like regular IOLs, LALs can shift and tilt during the few weeks long settlement process after implantation into the capsular bag. However, the shift or tilt of the LAL can be compensated by adjusting the optical properties of the implanted LAL. This adjustment can be achieved by illuminating the LAL with an ultraviolet (UV) light beam with a carefully selected spatial profile.

To prevent the UV portion of sunlight from modifying the optical properties of the LAL in the weeks between the implantation and the light adjustment procedure, the patients are asked to comply with the instruction of wearing UV blocking glasses. However, even a limited break in the compliance, such as the patient forgetting to put on the UV blocking sunglasses while going for a walk on a sunny day, can lead to uncontrolled and undesirable modifications of the optical properties of the LAL. U.S. Pat. Nos. 8,604,098 and 8,933,143, both entitled: "On-demand photoinitiated polymerization", both to Boydston et al. proposed introducing a "masking compound" to address this issue. As described below, however, these designs did not solve the challenge of unintended lens modifications caused by patient non-compliance. Therefore, there is still an unmet medical need for improvements in the Light Adjustable Lens technology that reduces and possibly eliminates the need for a strict patient compliance with the wearing of the UV blocking glasses.

SUMMARY

The above-described needs are addressed by embodiments of a modulable absorption light adjustable lens (MALAL), comprising: a light adjustable lens that is capable of changing its optical properties upon an adjusting irradiation, including a photo-modifiable material; and a modulable absorption front protection layer, including a modulable absorption compound whose absorption properties can be modulated with a modulating stimulus.

Other embodiments include a method of adjusting an optical property of a modulable absorption light adjustable lens, the method comprising: reducing an absorption of a modulable absorption compound of a modulable absorption front protection layer of the MALAL by a modulating stimulus, the MALAL having been previously implanted into an eye; and changing an optical property of a light adjustable lens of the MALAL by applying an adjusting irradiation.

BRIEF DESCRIPTION OF THE DRAWINGS

FIGS. 5A-F illustrate the steps of light adjustment of a MALAL 100.

DETAILED DESCRIPTION

This document describes embodiments of light adjustable intraocular lenses that provide improvements regarding the above described medical needs. The description starts by reviewing the Light Adjustable Lens technology in some detail.

Figure 1:
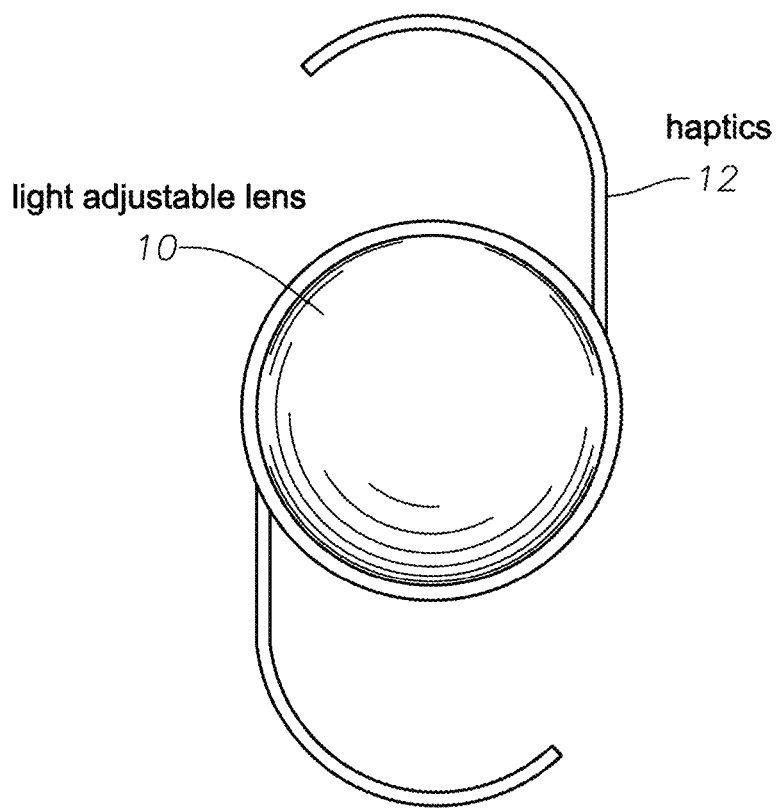
FIG. 1 illustrates a Light Adjustable Lens 10.

FIG. 1 illustrates a light adjustable lens (LAL) 10 that can be stabilized in the capsular bag by haptics 12 during the implantation. As mentioned earlier, in the weeks following the cataract surgery, the scarring and healing of the ophthalmic tissue can shift and tilt the LAL 10 away from its planned, optimal location inside the capsular bag. Also, the healing of the cornea can have significant impact on the resulting refraction. A key innovation of the LAL technology is that after the LAL 10 settles in the capsular bag, it is determined what adjustments of the optical properties of the LAL 10 can compensate this unplanned shift or tilt. This determination can involve objective measurements and the patient's subjective feedback. Then the LAL 10 is illuminated with an ultraviolet (UV) light with a spatial profile, or nomogram, selected to induce the determined adjustment of the LAL optical properties to compensate for the shift or tilt.

Given the sensitivity of the optical properties of the LAL 10 to UV light, in the weeks between the implantation and the adjustment, the patients are instructed to wear UV blocking spectacles to prevent the UV portion of the solar radiation from accidentally modifying the optical properties of the LAL 10. However, even a limited slip-up in the compliance, such as the patient forgetting to put on the UV blocking spectacles when going outdoors, can cause substantial changes in the optical properties of the LAL 10.

Figure 2:
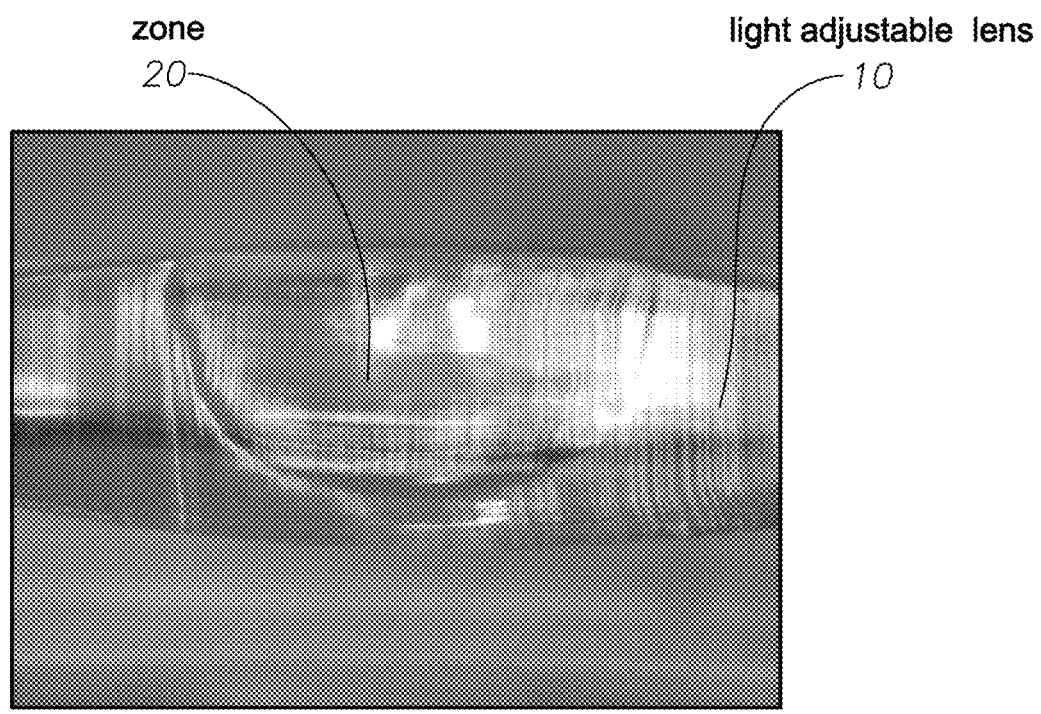
FIG. 2 illustrates the formation of zones with optical properties modified by excess UV radiation.

FIG. 2 illustrates the result of such non-compliance in some detail via cross section of the LAL 10 after it has been exposed to an incidental substantial UV illumination. The UV illumination photopolymerized the LAL 10 in a zone 20 with a substantial spatial extent and therefore adjusted the optical properties of the LAL 10 to a considerable degree in an uncontrolled manner, thus worsening the visual outcome.

FIGS. 3A-F illustrate embodiments of a modulable absorption light adjustable lens (MALAL) 100 that is suitable to prevent the formation of such undesirable zones in case of accidental non-compliance. The MALAL 100 in FIG. 3A can comprise a light adjustable lens LAL 110 that is capable of changing its optical properties upon an adjusting irradiation, the LAL 110 including a photo-modifiable material 111; and a moduable absorption front protection layer 120, that includes a modulable absorption compound 300, whose absorption properties can be modulated with a modulating stimulus. The optical properties of the LAL 110 can be adjusted by adjusting a shape of the LAL 110, a refractive property of the LAL 110, an index of refraction, an absorption property or a polarization property, or a combination of these properties of the LAL 110, thereby changing the optical properties of the MALAL 100 as well. The MALAL 100 can further include haptics 130, typically extending from the light adjustable lens 110. Embodiments of the haptics 130 can include 1, 2, 3, or more individual arms, extending from the LAL 110. In other embodiments, the haptics can be flat, flexible extensions of the LAL 110, with a rectangular or modified-rounded rectangular design. In some embodiments, the haptics 130 can extend from the modulable absorption front protection layer 120, or from an auxiliary structure.

To place the description of the MALAL 100 in context, first the Light Adjustable Lens LAL 110 will be described by itself in some detail in FIG. 4 and FIGS. 5A-F.

Figure 4:
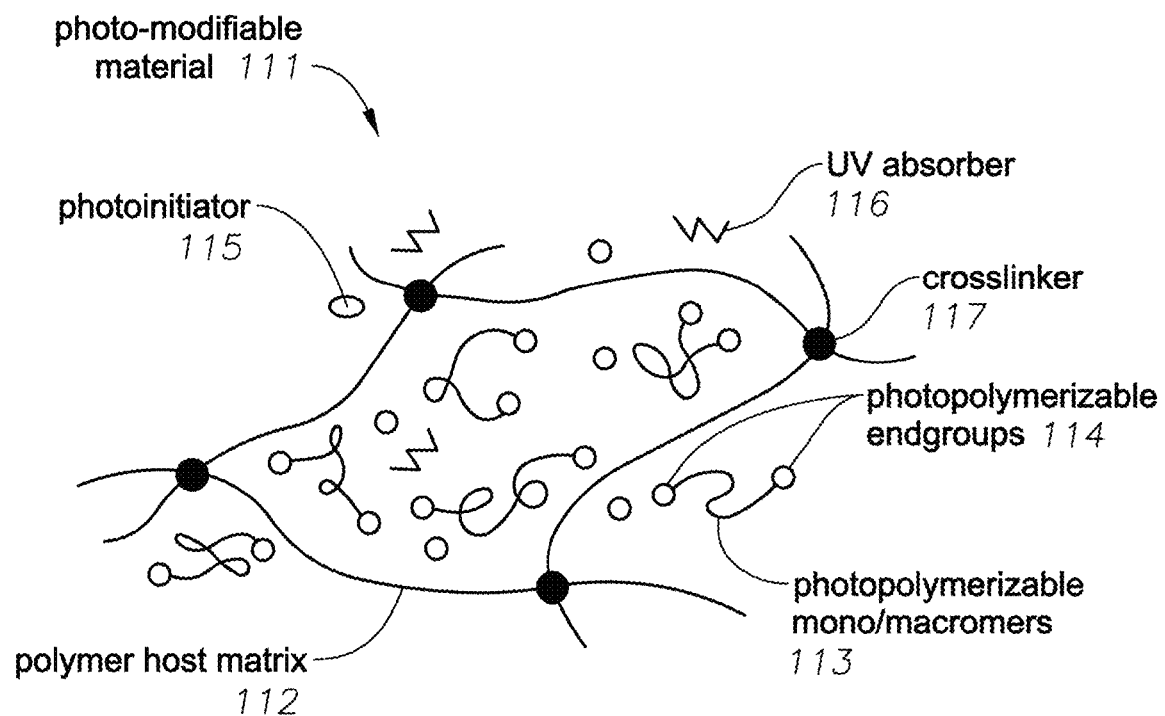
FIG. 4 illustrates the chemistry of the photo-modifiable material 111.

FIG. 4 illustrates that in the LAL 110 of the MALAL 100, the photo-modifiable material 111 can include a polymer host matrix 112. The polymer host matrix 112 can be a silicone-based matrix, an acrylate-based matrix, a collamer, a hybrid silicone-acrylate-based matrix, or a multi-layer matrix combining at least two of the preceding matrices.

In the LAL 110 of the MALAL 100, the photo-modifiable material 111 can further include photopolymerizable monomers or macromers 113, capable of photo-induced polymerization. These photopolymerizable monomers/macromers 113 can further include photopolymerizable endgroups 114. In addition, the photo-modifiable material 111 can include a photoinitiator 115 that can be either separate from the photopolymerizable monomers/macromers 113, or can be a functional group at the end of the photopolymerizable monomers/macromers 113.

The modulating stimulus, such as the aforementioned UV illumination, can activate the photoinitiator 115, which, in turn, can induce the photopolymerization of the photopolymerizable monomers/macromers 113, typically via their photopolymerizable endgroups 114. This photopolymerization process adjusts an optical property of the LAL 110, and thereby an optical property of the MALAL 100, as described below.

The LAL 110 of the MALAL 100 can further include a dispersed ultraviolet (UV) absorber 116. This UV absorber 116 can play different roles. One of them is to make sure essentially all incident UV illumination is safely absorbed inside the LAL 110, thereby providing retinal safety for the eye. Further, the UV absorber 116 can also play a role in controlling and shaping the spatially varying depth profiles of the MALAL 100.

Up to now embodiments of the MALAL 100 were described that were adjustable by a UV illumination as the adjusting irradiation. In other embodiments, the adjusting irradiation can involve other parts of the electromagnetic spectrum, such as specific portions of the UV spectrum, or infrared portions. Also, the adjusting irradiation can be an incoherent, or a coherent, laser-like, illumination, that can be applied simultaneously to large areas of the LAL 110, or sequentially, in a scanning manner.

FIGS. 5A-F illustrate the process of adjusting an optical property of the LAL 110 of the MALAL 100 in some detail. FIG. 5A illustrates that the first step of the LAL technology is the customary implantation of the LAL 110 into the eye of a cataract patient. FIG. 5B illustrates that the implanted LAL 110 can include the photopolymerizable monomers/macromers 113, embedded into the polymer host matrix 112. In the weeks following the implantation, the LAL 110 often shifts and tilts in the capsular bag, and in addition the corneal healing also impacts the optical properties of the eye, as described earlier. After a few weeks, once the LAL 110 settled in the capsular bag, the optical consequences of this shift, tilt, and corneal healing can be optically compensated by adjusting the optical properties of the LAL 110 by applying an adjusting irradiation 210. The adjusting irradiation 210 is applied with a spatial profile, sometimes called a nomogram, that is designed to induce the adjustment of the optical properties of the LAL 110 to compensate the shift and tilt of the LAL 110. In some embodiments, the adjusting irradiation 210 can be generated by a UV source, such as a mercury lamp, or a UV LED. The desired spatial profile can be achieved by deflecting or modulating the generated adjusting irradiation 210 with a Digital Mirror Device, or suitable alternatives.

FIG. 5C illustrates that the adjusting irradiation 210 can polymerize a spatially varying fraction of the photopolymerizable monomers/macromers 113 into photopolymerized macromers 113p (shown with bold lines) with the planned spatial profile.

FIG. 5D illustrates that the induced spatially varying density of polymerized macromers 113p induces a spatially varying density of the remaining unpolymerized monomers/macromers 113. This causes a spatially varying chemical potential that drives the unpolymerized monomers/macromers 113 to diffuse to the central region of the LAL 110. This diffusion causes a swelling of the central region of the LAL 110, and thus an increase of the optical power of the LAL 110, generating a hyperopic adjustment. The just described embodiments adjust the optical properties of the LAL 110 by adjusting its shape. For some classes of the photo-modifiable material 111, the adjusting irradiation 210 can adjust the optical properties of the LAL 110 in other ways, such as adjusting the index of refraction of the photo-modifiable material 111. Finally, in some embodiments, both the shape and the index of refraction of the photo-modifiable material 111 can be adjusted by the adjusting irradiation 210. Further, in cases when a myopic adjustment is desired, i.e. a reduction of the optical power of the LAL 110, the profile of the adjusting irradiation and thus the induced polymerization can be concentrated on the periphery of the LAL 110 instead of its center.

FIG. 5E illustrates the fact that after the adjusting irradiation 210 there will be leftover photopolymerizable monomers/macromers 113 that have not polymerized by the adjusting irradiation 210 and therefore may do so later when UV-containing ambient light reaches the LAL 110. Such a subsequent polymerization would cause uncontrolled and undesirable additional changes of the optical properties of the LAL 110. The LAL technology addresses this challenge by applying a lock-in irradiation 220 to the LAL 110 sometime after the adjusting irradiation 210 to polymerize essentially all remaining photopolymerizable monomers/macromers 113. This lock-in irradiation 220 is typically power neutral, i.e. is not meant to further adjust the optical properties of the LAL 110, as shown in FIG. 5F. In some cases, non-power-neutral lock-in irradiation 220 can be applied if the outcome of the adjusting process of FIG. 5B did not lead to the planned optical outcome for whatever reason. After essentially all the macromers 113 have been polymerized by the lock-in irradiation 220, subsequent exposure to sunlight or ambient light cannot induce further polymerization and further changes of the optical properties of the LAL 110. Thus, the steps described in FIGS. 5A-F make the LAL technology capable of delivering the optimal, planned optical outcome, in spite of potential LAL shifts and tilts, and corneal healing post implantation. This LAL adjustment process described in relation to FIGS. 5A-F was described in additional detail in commonly owned U.S. Pat. No. 6,905,641, entitled: "Delivery System for post-operate power adjustment of adjustable lens", to Platt et al., hereby incorporated in its entirety by reference.

As mentioned, the patients are instructed to wear UV blocking glasses through steps FIGS. 5A-E, until all photopolymerizable macromers 113 are photopolymerized by the adjusting irradiation 210 and the lock-in irradiation 220, to prevent unintended changes of the optical properties of the LAL 110. However, this requirement over the extensive period of weeks can be inconvenient for the patients, who may end up inadvertently breaking compliance, potentially causing undesirable optical changes in the LAL 110. Embodiments of the MALAL 100 offer an improved technology to ensure that the optical properties of the LAL 110 when included into the MALAL 100 remain under control even if the patient slips up with the compliance, such as he/she forgets to wear the UV blocking glasses.

Returning to FIG. 3A, the MALAL 100 additionally comprises the modulable absorption front protection layer 120, frontally positioned relative to the LAL 110, that includes a modulable absorption compound 300, whose absorption properties can be modulated with a modulating stimulus 310. The modulable absorption compound 300 can have a high-absorption conformation and a low-absorption conformation, wherein the modulable absorption compound 300 is capable of transforming from the high-absorption conformation to the low-absorption conformation upon absorbing a high-to-low modulating stimulus 310-*htl*. Further, the modulable absorption compound 300 is capable of transforming from the low-absorption conformation to the high-absorption conformation upon absorbing a low-to-high modulating stimulus 310-*lth*. For brevity's sake, where it does not lead to confusion, the high-to-low modulating stimulus 310-*htl* and the low-to-high modulating stimulus 310-*lth* together may be referred to simply as the modulating stimulus 310, even though they may be generated by different sources, since both of them modulate the absorption of the modulable absorption compound 300. Further, the modulable absorption compound 300 in its high-absorption conformation will be sometimes referred to as a high-absorption isomer 300-*h*, whereas the modulable absorption compound 300 in its low-absorption conformation will be referred to as a low-absorption isomer 300-*l*. In yet other cases, the modulable absorption compound 300 will be called a chromophore, its high-absorption conformation a high-absorption chromophore 300-*h*, and its low-absorption conformation will be referred to as a low-absorption chromophore 300-*l*.

When such a MALAL 100 is used in the LAL technology of FIGS. 5A-F, the MALAL 100 can be fabricated with the modulable absorption compound 300 of the modulable absorption front protection layer 120 in the high-absorption conformation and implanted in this state into the eye. By this fabrication method, the modulable absorption front protection layer 120 provides a strong protection for the photo-modifiable material 111 of the LAL 110 against accidental UV exposure in the weeks between steps FIG. 5A and FIG. 5B, potentially caused by non-compliance, such as forgetting to wear the UV blocking glasses. Here and subsequently, the light adjustment procedure will be described with reference to the steps shown in FIGS. 5A-F, where the LAL 110 will be meant to be the LAL 110 within embodiments of the MALAL 100.

Some embodiments of the MALAL 100 can provide more than protection from accidental non-compliance. Some MALALs 100 can be fabricated to provide strong enough protection such that wearing UV blocking glasses is not even necessary between the implantation and the lock-in of the MALAL 100. This benefit of the MALAL 100 is a great relief for the patients and doctors, alike as it increases the patient comfort, as well as essentially eliminates the risks and undesirable outcomes of inadvertent non-compliance. In these MALALs 100, a modulable absorption compound 300 is chosen that has a sufficiently high UV absorption, and the modulable absorption front protection layer 120 is chosen with a sufficiently large thickness so that these factors in combination provide sufficient protection of the photo-modifiable material 111 of the LAL 110 from the solar UV irradiation during the weeks between the implantation in FIG. 5A, through the adjustment procedure of FIG. 5B all the way to the lock-in of FIG. 5E so that the optical properties of the MALAL 100 do not change in spite of being exposed to the solar UV irradiation.

Once the MALAL 100 settled in the capsular bag, the time comes to adjust the optical properties of the LAL 110 of the MALAL 100, as previously outlined in FIG. 5B. In addition to the regular LAL technology, the procedure starts with first applying the high-to-low modulating stimulus 310-*htl* to transform the modulable absorption compound 300 from the high-absorption isomer 300-*h* to the low-absorption isomer 300-*l*. Before this transformation, an adjusting irradiation 210 would not have been able to pass through the high-absorption isomer 300-*h* of the modulable absorption front protection layer 120, but after this transformation into the low-absorption isomer 300-*l*, the adjusting irradiation 210 is capable of passing through the modulable absorption front protection layer 120 and reaching the LAL 110, and thus of adjusting its optical properties.

Figure 6:
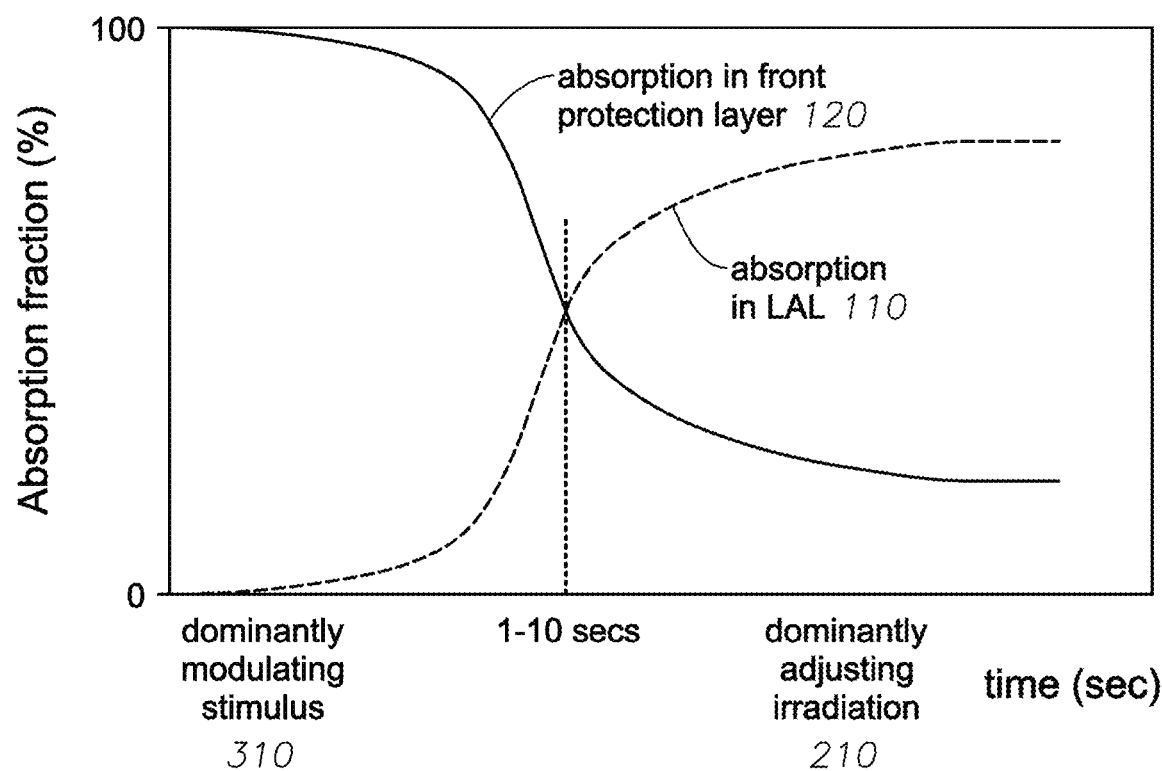
FIG. 6 illustrates the absorption of a single source illumination in the front protection layer 120 and the LAL 110 during a treatment.

As shown in FIG. 6, in some embodiments, a source of the modulating stimulus 310 can be the same as that of the adjusting irradiation 210, such as a mercury lamp or UV LED. In such single shared-source embodiments, the MALAL 100 can be illuminated by the UV beam from the shared-source that serves initially as a dominantly high-to-low modulating stimulus 310-*htl*, but as the illumination transitions the modulable absorption compound 300 from the high-absorption isomer 300-*h* into the low-absorption isomer 300-*l* in the front protection layer 120, an increasing fraction of the UV beam passes through the front protection layer 120 and reaches the LAL 110, thus increasingly acting as a dominantly adjusting irradiation 210, as shown. In some embodiments, the spatially varying profile of the illumination from the shared-source can be varied with time. In the initial time period when the illumination is dominantly a modulating stimulus 310, the spatial profile can be chosen to be a flat-top, largely independent of the radius to avoid an adjustment of the optical power of the LAL 110, while at later time when the illumination is dominantly the adjusting irradiation 210, the spatially varying profile can be switched to a power-adjusting profile, such as a polynomial or a gaussian, truncated at large radii as necessary. In other embodiments, the spatially varying profile can be power-adjusting over the entire time of the illumination. Finally, in yet other embodiments, the illumination can be applied with a flat-top profile while it is dominantly a modulating stimulus 310, then stopped, and then restarted with a power-adjusting profile for the time interval when it is dominantly the adjusting irradiation 210.

While until now embodiments of the MALAL 100 were described to be adjustable by a UV illumination being the modulating stimulus 310, in other embodiments the modulating stimulus 310 can take other forms, including an electromagnetic illumination, a laser irradiation, an infrared irradiation, an ultra-violet illumination, a magnetic stimulus, an electric field, a chemical stimulus, a heat transfer, an energy transfer, an ultrasound-mediated stimulus, a mechanical stimulus, a thermal stimulus, or a thermal relaxation.

Figure 3A:
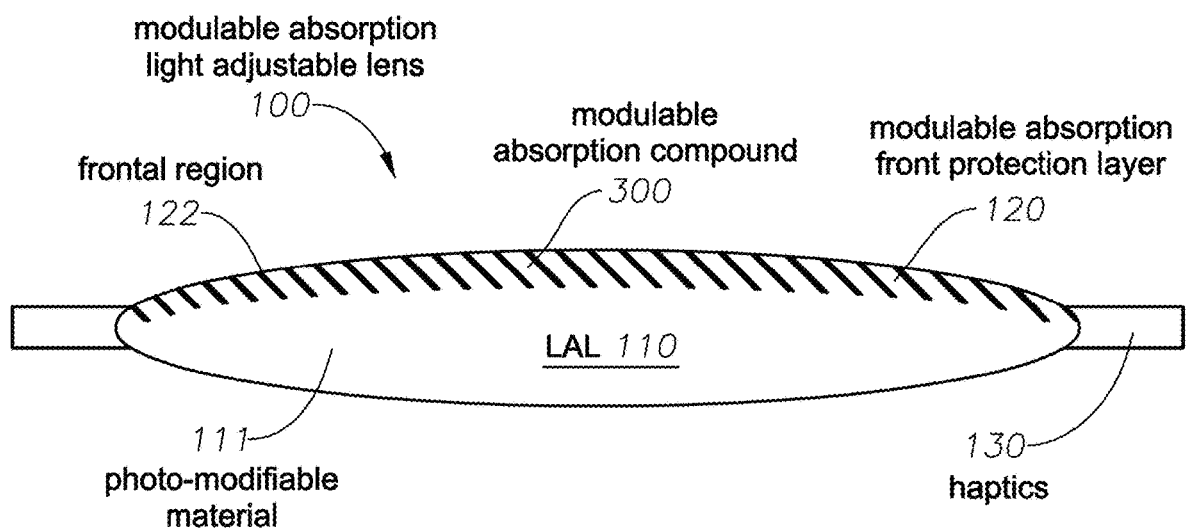
FIGS. 3A-F illustrate embodiments of a modulable absorption light adjustable lens (MALAL) 100.

FIGS. 3A-F illustrate that the front protection layer 120 can be frontally positioned relative to the LAL 110 in several different manner. In the embodiment of FIG. 3A, the modulable absorption compound 300 can be dispersed in a frontal region 122 of the light adjustable lens LAL 110, to form the modulable absorption front protection layer 120.

Figure 7A:
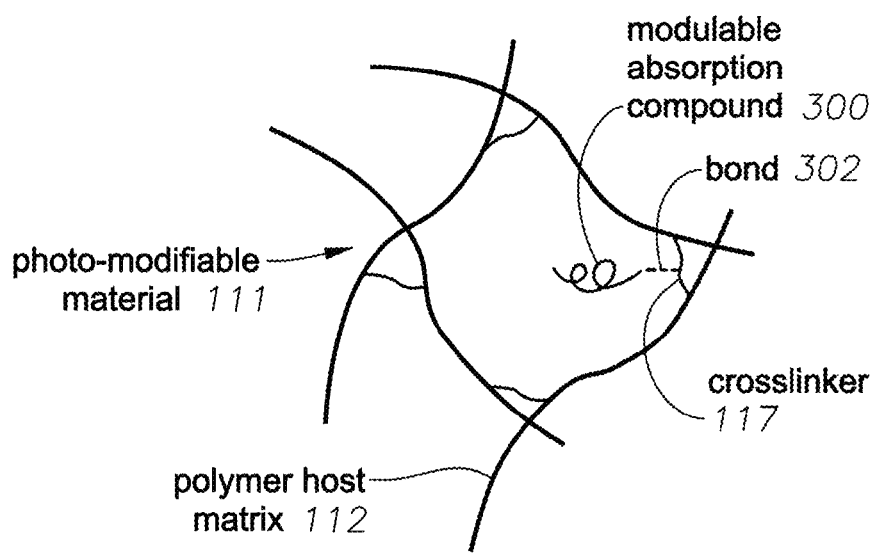
FIGS. 7A-D illustrate various ways the modulable absorption compound 300 can be related to the polymer host matrix 112.
Figure 7B:
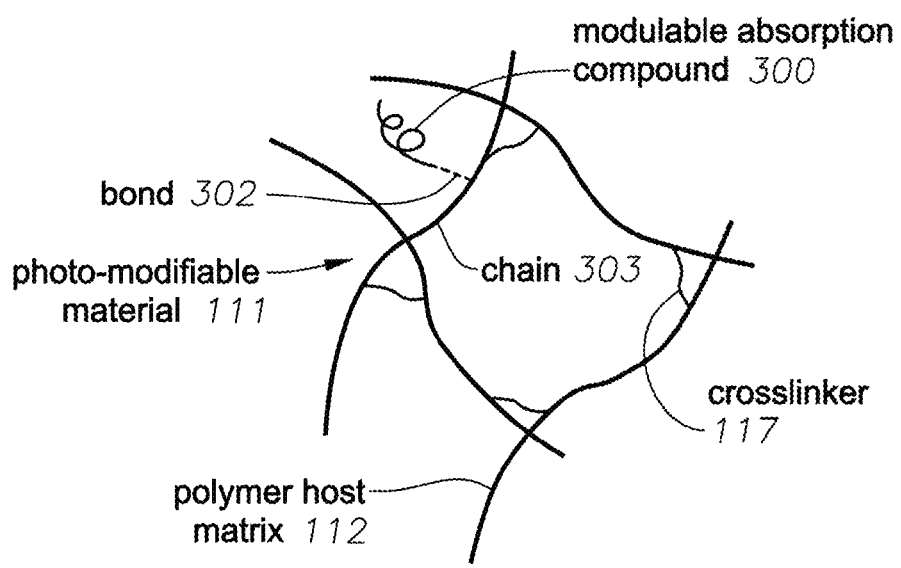

FIGS. 7A-D illustrate that the modulable absorption compound 300 can be localized to the polymer host matrix 112 in the frontal region 122 of the light adjustable lens 110 in various ways. FIG. 7A shows that the modulable absorption compound 300 can be localized to the polymer host matrix 112 by one or more bond 302 to the crosslinker 117 of the polymer host matrix 112, or to a chain 303 of the polymer host matrix, as shown in FIG. 7B. In such embodiments, the one or more bond 302 localizing the modulable absorption compound 300 can include a bond coupling a carbon or a silicon to a carbon, a silicon, an oxygen, a nitrogen, a hydrogen, a sulfur or a halogen atom.

Figure 7C:
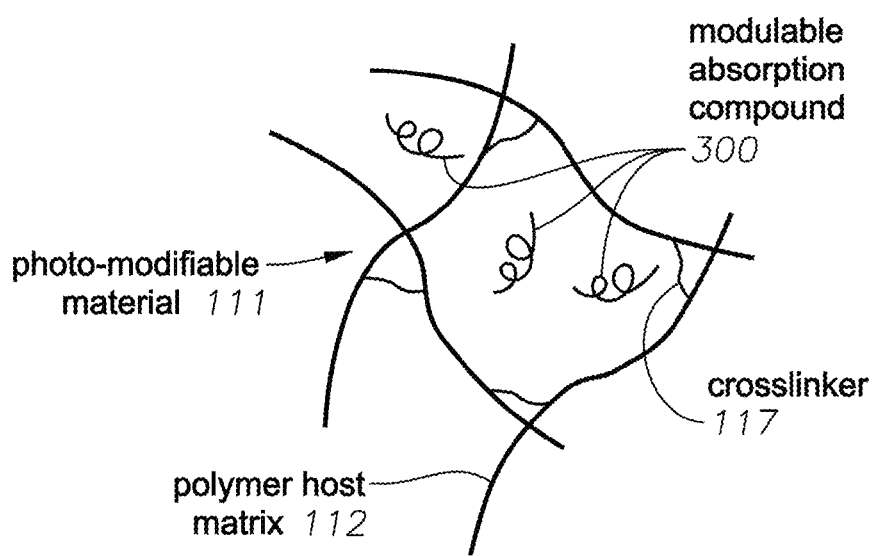
Figure 7D:
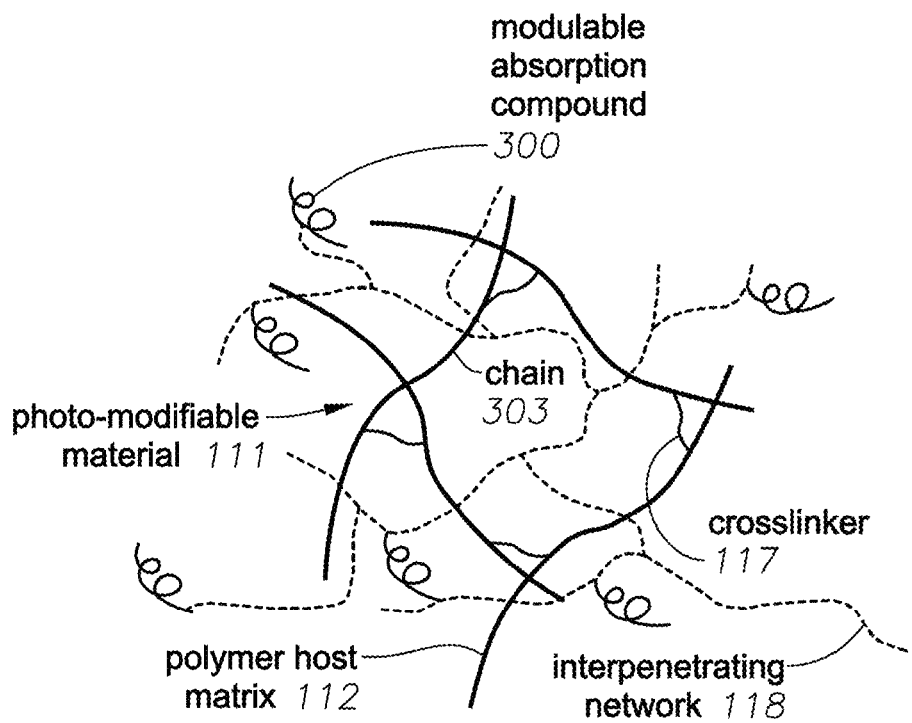

FIG. 7C illustrates that in some embodiments, the modulable absorption compound 300 can be mobile relative to the polymer host matrix 112, or can be a long chain polymer, interpenetrating the photo-modifiable material 111. Finally, FIG. 7D illustrates that the modulable absorption compound 300 can be bonded to an interpenetrating network 118 entangled into the polymer host matrix 112. The more mobile the modulable absorption compound 300 is relative to the polymer host matrix 112, the more likely an isolating layer is needed to prevent the modulable absorption compound 300 from diffusing either into the eye itself, or into the LAL 110.

Figure 3B:
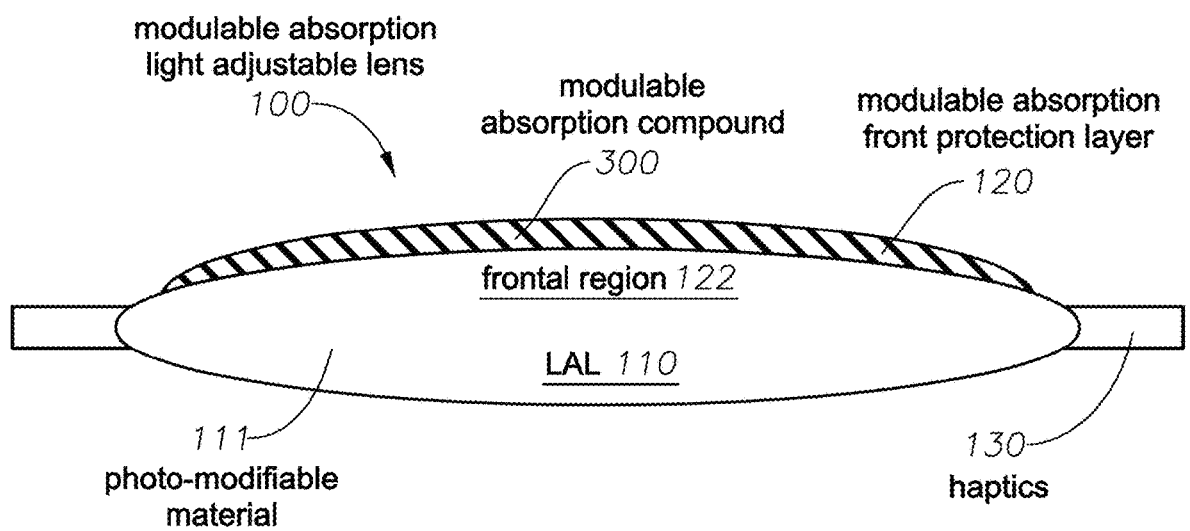

FIG. 3B illustrates that in other embodiments of the MALAL 100, the modulable absorption front protection layer 120 can be a layer attached onto the frontal region 122 of the light adjustable lens LAL 110, or a layer deposited onto the frontal region 122 of the light adjustable lens LAL 110. In these embodiments, the modulable absorption compound 300 is less likely to exhibit diffusion into the LAL 110.

Figure 3C:
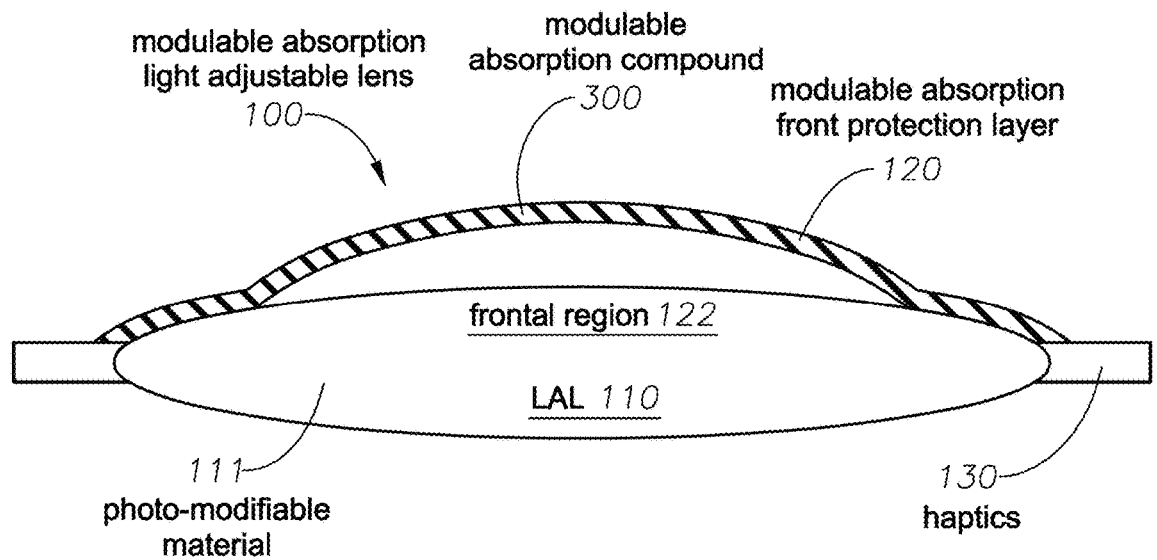

FIG. 3C illustrates that in some MALALs 100, the modulable absorption front protection layer 120 may be positioned in front of the light adjustable lens LAL 110, at least partially separated from it. Such embodiments provide an even clearer separation between the modulable absorption front protection layer 120 and the LAL 110, as well as further design features that can be optimized.

Figure 3D:
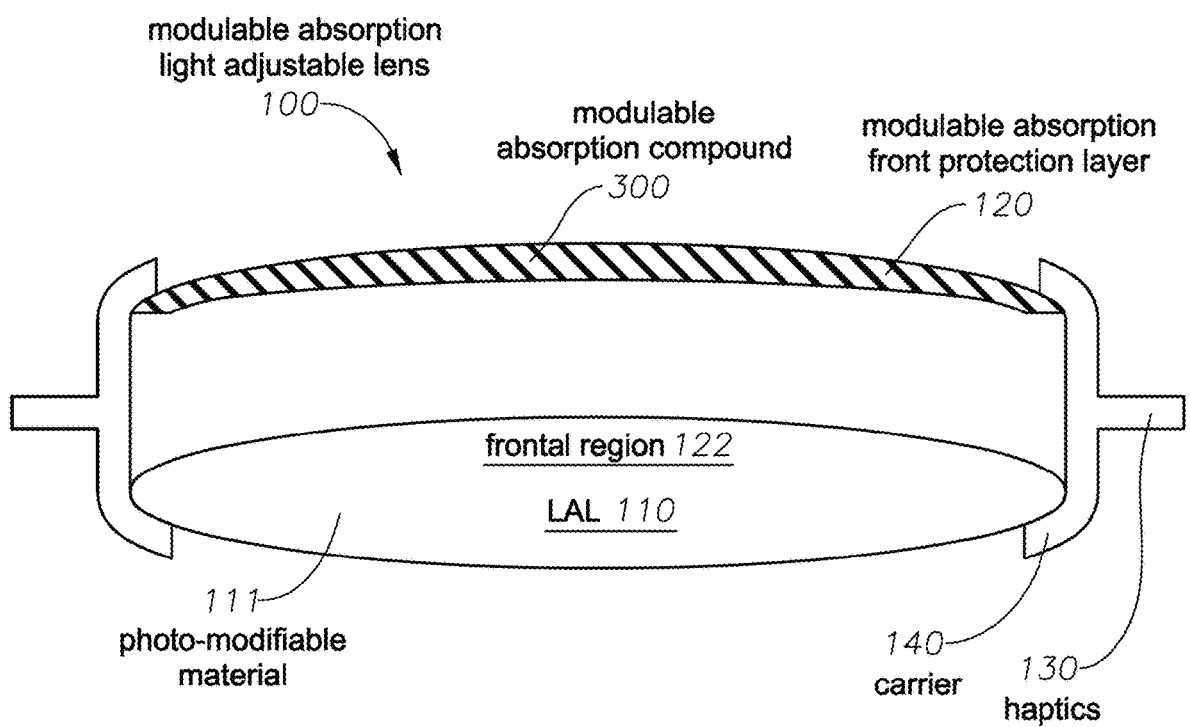

FIG. 3D illustrates that in some MALALs 100, the modulable absorption front protection layer 120 can be largely or completely separated from the LAL 110, and can be held in place by a carrier structure 140, or carrier 140 for short. The carrier structure 140 can have many different designs, including a posterior surface that has an opening, as shown, or no opening in other designs.

Figure 3E:
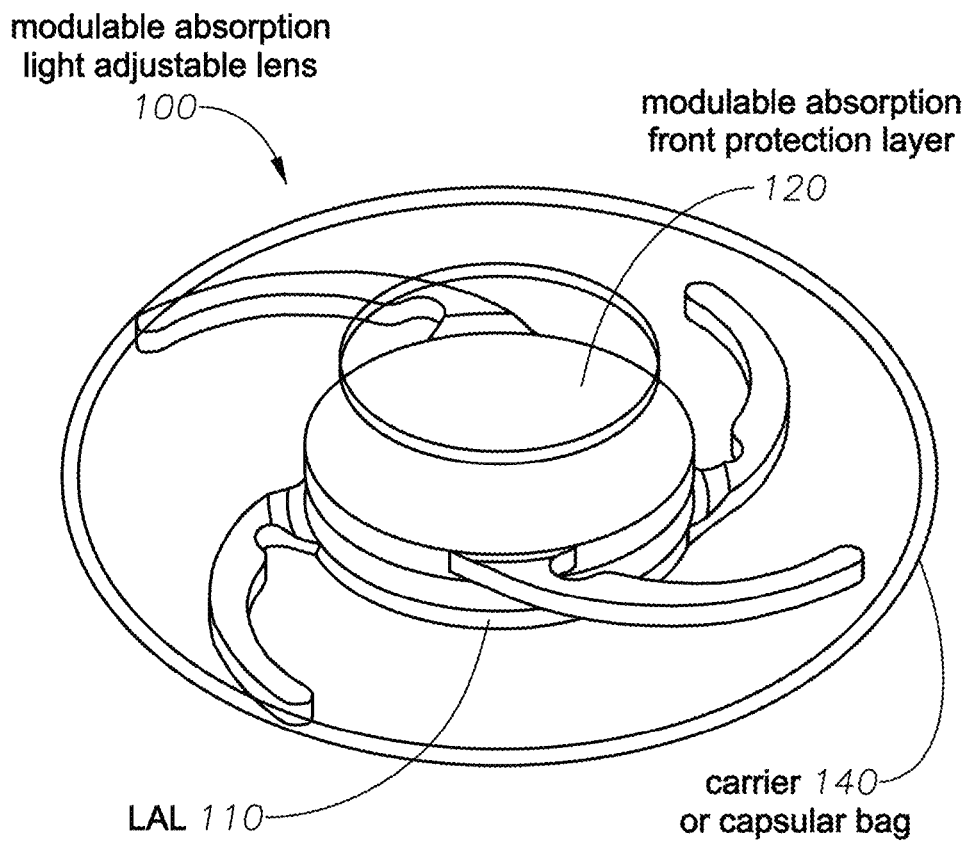
Figure 3F:
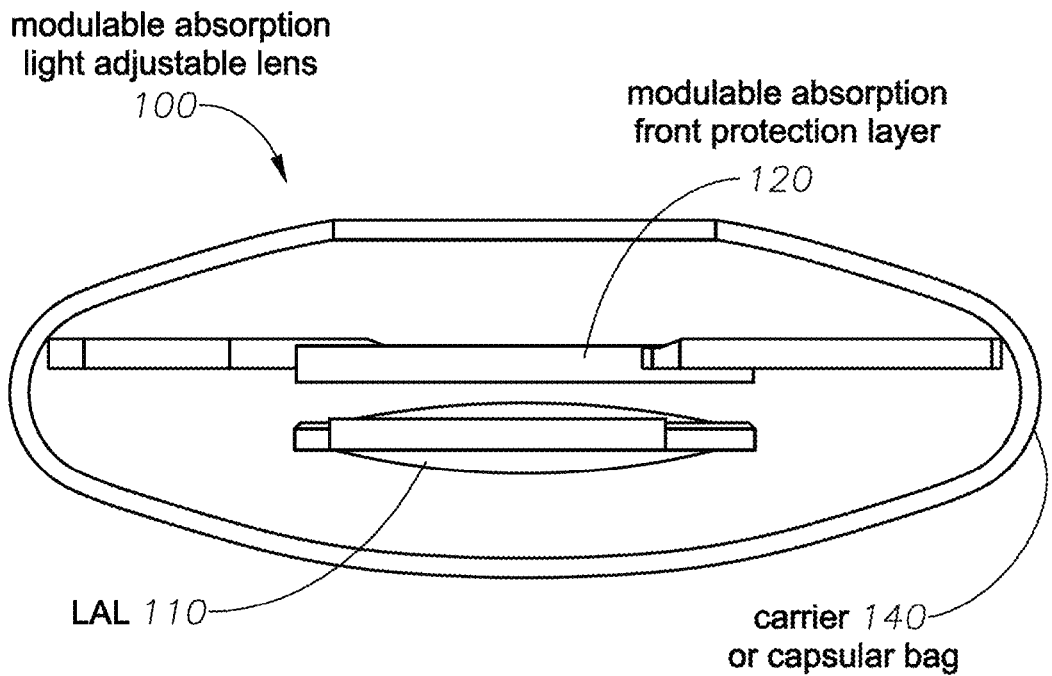

Finally, FIGS. 3E-F illustrate that in some implementations, the modulable absorption front protection layer 120 can be an independently insertable intraocular element. It may be inserted into a carrier 140, or in some embodiments, just inserted into the capsular bag in front of the LAL 110.

The physical extent of the modulable absorption front protection layer 120 can be characterized by a thickness that is less than 50%, 25%, 5%, or 2% of a thickness of the light adjustable lens LAL 110, in relative terms. In absolute terms, the thickness of the modulable absorption front protection layer 120 can be in the range of 1-200 microns, in some cases in the range of 1-100 microns, in yet others in the range of 10-50 microns.

Before proceeding, we return to U.S. Pat. Nos. 8,604,098 and 8,933,143, both entitled: "On-demand photoinitiated polymerization", both to Boydston et al. These patents proposed introducing a "masking compound" into light adjustable lenses to reduce the risk of unintended polymerization until the time of the light adjustment, at which time a photoisomerization was triggered to allow the adjustment of the lens. However, the solution offered by these patents did not solve the problem, as the masking compound was broadly distributed throughout the volume of the light adjustable lens. Because the masking compound was dispersed throughout the volume of the lens, the frontal region of the light adjustable lens did not get sufficient protection and was prone to undesirable zone formation and thus to uncontrolled and undesirable changes of its optical properties.

Embodiments of the MALAL 100 deliver where this previous proposition failed, by concentrating the protective modulable absorption compound 300 in the front protection layer 120, formed and positioned frontally relative to the LAL 110, instead of dispersing the compound 300 throughout the volume of the LAL 110. This is the structural improvement that enables the MALALs 100 to provide full protection from UV rays for even the most frontal region of the LAL 110, because only this frontal positioning of the protective modulable absorption compound 300 prevents the accidental zone formation and the uncontrolled optical changes from the implantation, through the adjustment, until the lock-in of the MALAL 100.

Figure 8B:
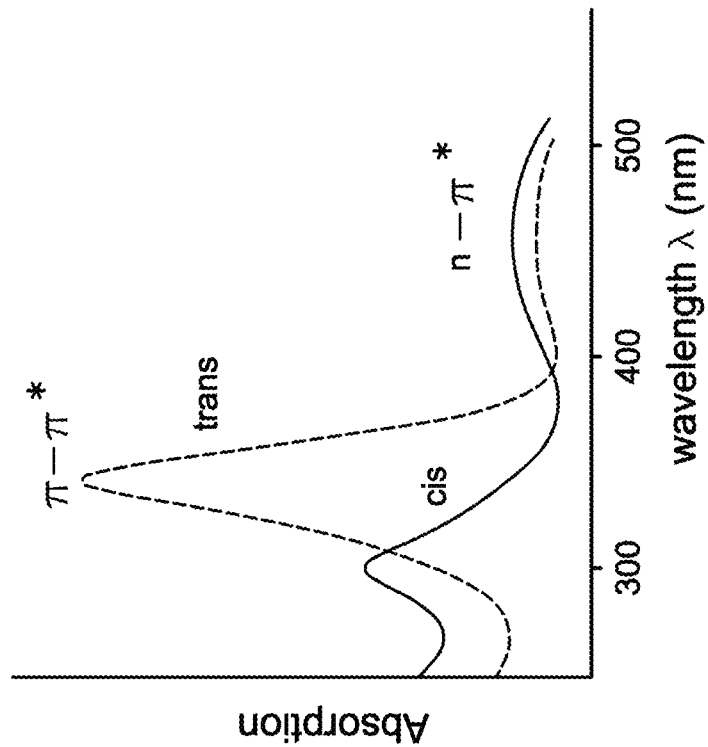
FIGS. 8A-B illustrate the chemical composition and absorption spectrum of azobenzene.
Figure 8A:
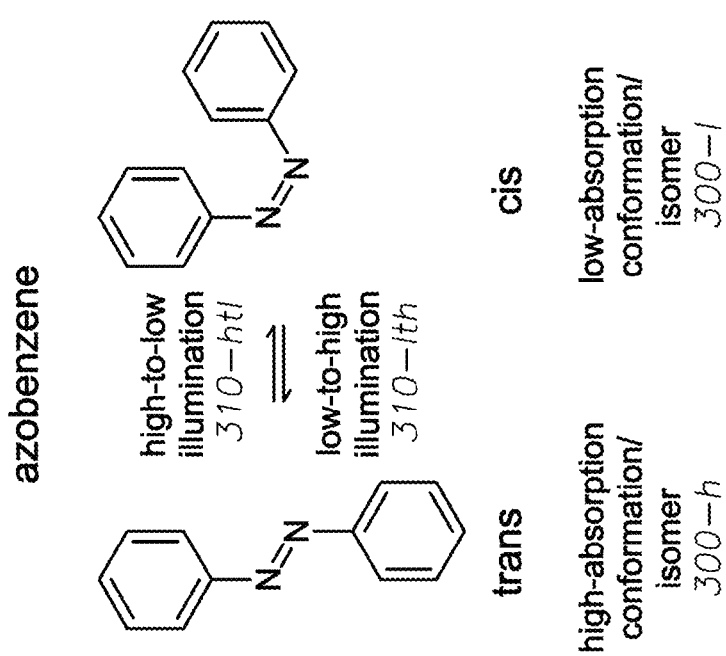

FIGS. 8A-B continue the description of embodiments of the MALAL 100 by identifying and describing specific examples of the modulable absorption compound 300. For specificity, the description starts with detailing a particular example, followed by a large number of alternative solutions. Azobenzene is one of the compounds known to change its absorption properties upon stimulation by light. Azobenzene is one of the simplest examples of the family called azo compounds by the general form of R—N=N—R', where R and R' can be an aryl or an alkyl, or groups of these. Azobenzene is known to have two conformations, differing in the bond angle between the N=N double bond and one of the two phenyl rings. The "trans" conformation has high absorption in the UV spectrum, with a peak in the 360-370 nm wavelength range, where the absorption involves a π-to-π*electronic transition. An analogous absorption peak is present in a variety of functionalized azobenzenes as well. A UV light with a wavelength around 365 nm can serve as the high-to-low modulating stimulus 310-*htl*, to transform the azobenzene from its high-absorption isomer 300-*h* with trans conformation to its low-absorption isomer 300-*l* that has a cis conformation. As shown, the cis conformation has a much lower absorption around 365 nm wavelength. Therefore, azobenzene is an embodiment of the modulable absorption compound 300 of the front protection layer 120 that largely blocks incoming UV rays in its trans conformation 300-*h*, but can be switched into the low absorption cis conformation 300-*l* to let the adjusting radiation 210 through to the LAL 110. For completeness, it is mentioned that azobenzene-based compounds can have additional conformations.

As already described in relation to FIG. 6, when a UV light is used to illuminate the MALAL 100, it first acts dominantly as the high-to-low modulating stimulus 310-*htl* and transforms an increasing fraction of the azobenzene modulable absorption compound 300 from its high-absorption trans isomer 300-*h* to its low-absorption cis isomer 300-*l*. As the UV illumination continues to modulate the absorption of the azobenzene by inducing the trans-to-cis transformation, an increasing fraction of the UV beam passes through the front protection layer 120 and reaches the LAL 110, where it acts as the adjusting irradiation 210 and thus changes the optical properties of the LAL 110. The UV illumination can be applied with a spatial profile, or nomogram, that brings about the planned adjustment of the optical properties of the LAL 110.

Once the UV beam as the adjusting irradiation 210 has been applied with the spatial profile needed to eventually induce the adjustment of the optical properties of the LAL 110, as related to FIG. 5B, the diffusion of the photopolymerizable macromers 113 starts, as shown in FIGS. 5C-D. However, since this diffusion can take a day or longer, the MALAL 100 once again needs to be protected from uncontrolled UV illumination until the lock-in irradiation 220 of FIG. 5E is applied. This protection can be achieved by applying a low-to-high modulating stimulus 310-*lth* to transform the low-absorption isomer 310-*l* back to a high-absorption isomer 300-*h*. In the case of the azobenzene, this translates to transforming the cis conformation back into the trans conformation. Doing so can be achieved by applying a low-to-high modulating stimulus 310-*lth* that has substantial spectral weight around the absorption maximum of the low-absorption cis isomer 300-*l*.

FIG. 8B illustrates that the low-absorption cis isomer 300-*l* has its absorption peak around 450 nm that involves an n-to-π*electronic transition. Thus, an illumination that has a strong spectral weight around 450 nm can serve as the low-to-high modulating stimulus 310-*lth* and can induce a cis-to-trans transformation, to re-establish the UV protection for the underlying LAL 110.

Applying the low-to-high modulating stimulus 310-*lth* with (1) a dedicated light source, may be helpful for some embodiments, but in some others, it is not necessary. At least the following other agents can bring the cis conformation 300-*l* back to the trans conformation 300-*h*. (2) Thermodynamic relaxation, since the trans conformation has lower energy than the cis conformation, and therefore thermodynamic relaxation efficiently restores the azobenzene into its initial trans conformation. (3) Sunlight, or ambient light by itself can act as an efficient accelerant, to drive azobenzene into a driven steady state with high concentration of the trans conformation, as described next in detail.

In general, the full description of photoisomerization can be thought of as a dynamic balance of a trans-to-cis and a cis-to-trans reaction:

Reaction R

$$\text{VPAP}_{trans} + h\nu \rightarrow \text{VPAP}_{cis} R_t \tag{1a}$$

$$\text{VPAP}_{cis} + h\nu \rightarrow \text{VPAP}_{trans} R_c \tag{1b}$$

Here the reaction rates can be defined by the spectral integrals as follows:

$$R_t = \int_{\lambda_{t1}}^{\lambda_{t2}} \left(\frac{\lambda}{h \cdot c}\right) \varphi_t I_s(\lambda) \varepsilon_t(\lambda) \ln(10) c_t d\lambda \tag{2a}$$

$$R_c = \int_{\lambda_{c1}}^{\lambda_{c2}} \left(\frac{\lambda}{h \cdot c}\right) \varphi_c I_s(\lambda) \varepsilon_c(\lambda) \ln(10) c_c d\lambda + R_{therm} \tag{2b}$$

Here $\varphi_t$ and $\varphi_c$ are the quantum yields of absorption, defined as photo-induced transition/absorbed photon, and are thus dimensionless. The wavelength dependence of these quantum yields in the relevant wavelength interval is minimal and will be disregarded. $I_s(\lambda)$ is the spectral irradiance of the incident radiation, in units of [power/(area*wavelength)], such as [mW/(cm$^2$*nm)]. The trans-to-cis absorption, related to the π-π*transition, is induced by absorbing photons in the $\lambda_{t1}$-$\lambda_{t2}$ range, while the cis-to-trans absorption, related to the n-π*transition, is induced by absorbing photons in the $\lambda_{c1}$-$\lambda_{c2}$ range—these two wavelength intervals will be also referred to as absorption bands and constitute the boundaries of the integrals. $\varepsilon_t(\lambda)$ and $\varepsilon_c(\lambda)$ are the molar absorptivity values in the trans and cis states, respectively, in units of [volume/(mol*length)], such as [liter/(mol*cm)]; and $c_c$ and $c_t$ are the concentrations of the modulable absorption compound 300 in its low-absorption cis and high-absorption trans conformations, in the usual units of [mol/liter]. The molar absorptivities can be also thought of as absorption cross sections. Eqs. (2a)-(2b) yield the reaction rates $R_t/R_c$ in units of [(1/sec)*(reactions/cm)], which are related to the inverse time constants $k_t/k_c$ via the concentrations $c_t/c_c$. $R_{therm}$ is the rate at which the cis state thermally decays into the trans state. $R_{therm}$ can be estimated as $k_{therm}*c_c$, where $k_{therm}$ can be defined as the inverse of the 1/e time constant for thermal relaxation. In some typical compounds, $k_{therm}^{-1}$ is typically in the range of 1-20 hours, in some cases as long as 1-5 days, but can also be 10-1,000 seconds. In the presence of a low-to-high modulating stimulus 310-*lth*, including even ambient light, the $R_{therm}$ term is typically 2 or 3 orders of magnitude smaller than the integral term, and will be disregarded for the current analysis. Further, the concentration of the trans conformation is given by $c_t$, while the concentration of the cis conformation by $c_c$. Naturally, $c_t+c_c=c_0$, the total concentration of the modulable absorption compound 300, in this case, that of azobenzene that does not change with time. The speed of light is denoted by simply c, and Plank's constant by h. With these constants, the $\lambda/hc=1/hv$ term divides the spectral irradiance $I_s(\lambda)$ with its energy h v, thereby converting the spectral irradiance from power density to photon number density.

In a steady-state, dynamic equilibrium the trans-to-cis and the cis-to-trans rates are equal $$R_t=R_c \qquad (3)$$

which relation determines the ratio of the cis and trans concentrations in this dynamic equilibrium as:

$$a \equiv \frac{c_t}{c_c} = \frac{\varphi_c \int_{\lambda_{c1}}^{\lambda_{c2}} \lambda I_s(\lambda)\varepsilon_c(\lambda)d\lambda}{\varphi_t \int_{\lambda_{t1}}^{\lambda_{t2}} \lambda I_s(\lambda)\varepsilon_t(\lambda)d\lambda} \qquad (4)$$

which yields for the individual cis and trans concentrations the following relationships:

$$c_c = \frac{c_0}{1+a} \qquad (5a)$$

$$c_t = \frac{a \cdot c_0}{a+1} \qquad (5b)$$

These results are approximate, as they capture the situation when the illumination spectral irradiance $I_s(\lambda)$ is incident on the modulable absorption compound 300, so they hold close to the surface, or for a thin modulable absorption front protection layer 120. For modulable absorption front protection layers 120 extended in the z, or depth direction, the spectral irradiance decays with increasing z depth as it propagates through the front protection layer 120. A more complete treatment captures the effect of this decay on the absorption in terms of a z-depth dependent spectral irradiance $I_s(\lambda,z)$ and integrates the rates of the absorption processes along the z-depth. The results of such an in-depth analysis are often well approximated by the above formulae. The influence of the depth-dependence of the irradiance will be further analyzed below.

First, the case of the high-to-low modulating stimulus 310-*htl* will be considered. In a typical case, such a stimulus 310-*htl* can be applied by a powerful UV light source, such as a mercury lamp or a UV LED. Such sources often generate an illumination with a quite narrow band. This can be approximated by a Dirac delta which is taken to be centered at the standard wavelength $$a_{LDD} = \frac{\varphi_c \varepsilon_c(365\,\text{nm})}{\varphi_t \varepsilon_t(365\,\text{nm})} \qquad (6)$$

of mercury lamps, 365 nm, thereby simplifying the integrals into products, and yields the simple expression for the concentration ratio a of such a Light Delivery Device LDD:

For azobenzene, $\varphi_t \approx 0.15$ and $\varphi_c \approx 0.5$; and the ratio of the molar absorbances is about 0.1, yielding $a_{LDD} \approx 0.3$. This means that applying a UV light source as the source of the high-to-low modulating stimulus 310-*htl* induces a dynamical equilibrium in which the concentration $c_t$ of the trans conformation is about one third of that of $c_c$, the concentration of the cis conformation, so only approximately 25% of the modulable absorption compound 300 will remain in the trans conformation compared to the approximately 100% initial concentration. This about 4-fold reduction of the trans conformation concentration is sufficient to let a large portion of a subsequent adjusting irradiation 210 through the front protection layer 120 into the LAL 110 for a suitably chosen thickness of the front protection layers 120. One aspect of the above derivation worth articulating explicitly is that the application of the high-to-low modulating stimulus 310-*htl* does not switch all high-absorption isomers 300-*h* into low-absorption isomers 300-*l* in full, much rather a partial modulation and transformation is the result.

Next, the reverse process, the low-to-high modulating stimulus 310-*lth* is described in a particularly simple case, when no explicit light source is applied, but, rather, simply the ambient light is allowed to control the concentrations of the two conformations. For this case, the spectral irradiance $I_s(\lambda)$ is that of the solar radiation in case of a direct exposure, i.e. the patient looks directly into the Sun. The concentration ratio a remains the same for indirect, diffuse exposure, when only the diffused sunlight reaches the eye, since Eq. (4) that governs the concentration ratio is controlled only by the ratio of the solar irradiances, and from this ratio the effect of diffusion cancels out.

The magnitude of the solar irradiance below 300 nm wavelength which reaches the IOL is negligible because the cornea efficiently absorbs UV light for shorter wavelengths, and the molar absorption above 500 nm, of azobenzes and related compounds under consideration, is likewise negligible. Therefore, the integrals in Eq. (4) are executed over the $\lambda=300$ nm-500 nm wavelength range with the solar spectral irradiance, yielding:

$$a_{solar} = \frac{\varphi_c \int_{300\,nm}^{500\,nm} \lambda I_s(\lambda)\varepsilon_c(\lambda)d\lambda}{\varphi_t \int_{300\,nm}^{500\,nm} \lambda I_s(\lambda)\varepsilon_t(\lambda)d\lambda} \qquad (7)$$

Eq. (7) yields for some azo compounds and others described below an a concentration ratio of about 3. For some other modulable absorption compounds 300, a is in the range of 5-10. These values translate to a trans conformation concentration of $c_t=75\%$ for a=3, and $c_t=84$-91% for a=5-10. Front protection layers 120 with the modulable absorption compound being in its high absorption conformation 300-*h* in concentrations in the 75-91% range, can provide robust UV protection for the underlying LAL 110.

For completeness, several different embodiments low-to-high modulating stimulus 310-*lth* can be employed for various MALALs 100. (1) As discussed here, the patient simply being exposed to ambient light can increase the concentration of the high-absorption isomer 300-*h* back to levels where it can serve as an efficient front protection layer 120. For front protection layers of thickness 10-100μ, in some cases 20-50μ, and overall molar concentrations of $c_0$ in the 10-100 millimolar range, in some cases in the 20-30 millimolar range, the time for this concentration increase can be in the 1-10 seconds range. Such a switching time can be naturally accommodated in the ophthalmologist office after the adjusting step of FIG. 5B or the lock-in step of FIG. 5E, without the risk of an uncontrolled zone formation in the LAL 110 in this very short time. (2) In other embodiments, a dedicated light source can be used as the source of the low-to-high modulating stimulus 310-*lth* to induce a switching transition back to the high-absorption isomer 300-*h* even faster. For example, a solar simulator, a white flashlight, or a stronger illumination source can be employed, potentially with a UV filter to maximize the 300-$l$-to-300-$h$ conversion rate. (3) Finally, because the energy of the high-absorption isomer 300-$h$ is lower than that of the low-absorption isomer 300-$l$, simple thermal relaxation also returns the modifiable absorption compound to the protective high-absorption conformation 300-$h$. As mentioned before, this process can be about a hundred times slower for azobenzene, but this still only translates into minutes without any express low-to-high modulating stimulus 310-$lth$. Thus, leaving the patient in a simple office-light condition for a couple minutes after the procedure can also restore the protective effect of the front protection layer 120.

The above considerations indicate that modulable absorption compounds 300 that have a concentration ratio a<<1 for a narrow bandwidth UV modulating stimulus 310-$htl$, while at the same time have a concentration ratio a>>1 for solar radiation, or an explicit low-to-high modulating stimulus 310-$lth$, are well-suited to provide two beneficial effects: (1) such modulable absorption compounds 300 are capable of protecting the MALAL 100 from uncontrolled optical adjustments caused by involuntary patient non-compliance from implantation to lock-in; (2) while at the same time they are capable of enabling the application of adjustment illuminations 210 by a conformation change, induced by a modulating stimulus 310.

Now we return to the issue of the spectral irradiance decaying with increasing z-depth. Remarkably, this decay only increases the utility of the MALALs 100, because it induces a "self-shielding effect". In the informative embodiment of ambient solar irradiation acting as the low-to-high modulating stimulus 310-$lth$, as the solar irradiation propagates deeper and deeper into the front protection layer 120, the UV portion of the solar irradiation $I_s(\lambda,z)$ is absorbed faster than the visible portion. This is so because in the presence of a realistic amount of trans high-absorption isomer 300-$h$, such as the previously determined $c_t$>25%, the absorptivity is higher in the UV range than in the visible range. For specificity, in typical modulable absorption compounds 300 which contain both trans high-absorption isomers 300-$h$ and cis low-absorption isomers 300-$l$, this translates to $\varepsilon(\lambda=365\text{ nm})>\varepsilon(\lambda=450\text{ nm})$. Inspection of Eq. (7) for the concentration ratio $a_{solar}$ reveals that as the spectral irradiance $I_s(\lambda,r)$ decays faster in the UV range, $a_{solar}$ increases faster. In a simplified explanation, deeper in the front protection layer 120 there are less and less UV photons to transform the modulable absorption compound 300 from the trans high-absorption isomer 300-$h$ to the cis low absorption isomer 300-$l$, while in relative terms more and more visible photons are driving the reverse process from the cis low-absorption isomer 300-$l$ to the trans high-absorption isomer 300-$h$, thereby increasing $a_{solar}$ with increasing depth, further increasing the overall protective UV blocking functionality of the front protection layer 120.

One more aspect of the depth-dependence of the spectral irradiance is articulated next. The overall reduction of the spectral irradiance exiting the front protection layer 120 through its distal surface is controlled by the absorbance that is given by the product of $\varepsilon$, the molar absorptivity of the modifiable absorption compound 300, c, the molar concentration of the modifiable absorption compound 300, and D, the thickness of the front protection layer 120. In optical design terms, the absorbance is sometimes also referred to as optical density. Thus, different embodiments of the front protection layer 120 that contain different modulable absorption compounds 300 with different molar absorptivities in different molar concentrations and with different thicknesses, will deliver approximately the same protection, as long as the product of these three quantities is the same. The eventual choice of the modulable absorption compound 300, its concentration and its thickness can be driven by additional considerations, such as the desire to avoid an excessive yellowing of the visual experience for the patient.

Before proceeding, it is useful to summarize the potential benefits of MALALs 100 with the above front protection layer 120 relative to existing designs, some of which were already mentioned earlier.

(1) MALALs 100 with front protection layer 120 greatly reduce the risk of uncontrolled optical changes in the LAL 110 resulting from accidental non-compliance by the patients, such as forgetting to wear the UV blocking glasses.

(2) Further, in MALALs 100 a considerably lower concentration of the UV absorber 116 can be employed that is dispersed in the volume of the LAL 110. Such LALs 110 require a substantially lower dose for the lock-in irradiation 220. Any reduction of the dose of the UV lock-in irradiation of the MALAL technology further enhances the safety of the procedure.

(3) MALALs 100 with a more absorbing front protection layer 120 can even provide such an effective UV blocking that the patients may not even need to wear UV blocking glasses from the implantation through the adjustment up to the lock-in. This is greatly beneficial as such MALALs 100 essentially eliminate the risks caused by accidental patient non-compliance, as well as greatly improve patient comfort from implantation to lock-in.

(4) MALALs 100 with even more absorbing front protection layers 120 may not even need the lock-in step of FIG. 5E. The UV blocking by the front protection layer 120, once it is restored into its high-absorption isomer 300-$h$ after the adjusting radiation 210, can be so efficient and so robust, that it can fully prevent UV radiation entering the LAL 110 for very long periods, such as years and decades. In such highly protective MALALs 100, even though their LAL 110 may contain a notable concentration of non-polymerized photopolymerizable monomers and macromers 113 left over from the adjustment step of FIG. 5B, the robust, long-term UV absorption by the front protection layer 120 can ensure that the non-polymerized monomers and macromers 113 will not be photopolymerized by the solar irradiation for years and decades, and thus the MALAL 100 will reliably preserve and deliver the optical performance that was formed by the adjusting irradiation 210 during the adjusting step of FIG. 5B. Such "no lock-in" MALALs may reduce the number of visits required from the patient to a single adjusting procedure.

(5) Even more remarkably, in a fraction of patients the implanted MALAL 100 may not even shift or tilt. Such patients may report that after the implantation their vision remained high quality and did not deteriorate noticeably. For these patients, the doctor may even conclude that not even one follow-up visit is needed for adjusting the MALAL 100. For all those patients who would need a longer trip for the adjustment and/or lock-in procedures, possibly even involving an airplane flight, the likelihood of no need for any kind of follow-up visit can mean a further qualitative improvement in their overall experience, or "journey".

(6) Finally, in a small subset of cases, unforeseen changes may occur in the eye long after the cataract surgery, caused by various other ophthalmic degradation, injuries or any kind of shocks. In such cases, the fact that the no lock-in MALAL 100 remains adjustable can be very beneficial, as such MALALs 100 can be adjusted in response to the unforeseen developments even years after the implantation.

There are many other embodiments of the modulable absorption compound 300 beyond azobenzene. The modulable absorption compound 300 can be an azo-aromatic compound, a diazene, an azo-pyrazole, a dienylethene, a fulgicide, an azulene, a spiropyran, an ethene-aromatic compound, a macromer of one of these compounds, a polymer of these compounds, a composition containing one of these compounds, a composition containing one of these compounds as side-chains, a composition containing one of these compounds as a backbone having a side-chain, a nanoparticulate bonded to one of these compounds; and one of these compounds dissolved in an ionic fluid. The modulable absorption compound 300 could also be a polymer incorporating any of the just listed compounds into the polymer host matrix 112 itself, so it doesn't have to be incorporated as a side chain. Some such compounds may include a polymer which bends in response to light. The description continues by overviewing an extensive list of embodiments of the modulable absorption compound 300.

As mentioned earlier, the azo-aromatic compound can be e.g. azobenzene that exhibits the following conformational change [1]:

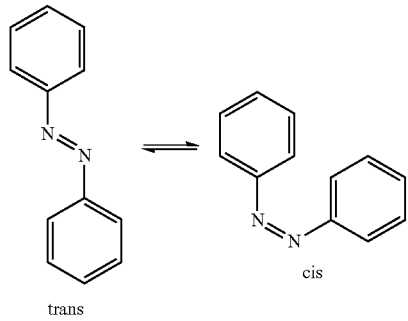

[1]

trans    cis

In other embodiments of the modulable absorption compound 300, the azo-aromatic compound can be 4-methoxy azobenzene [2]:

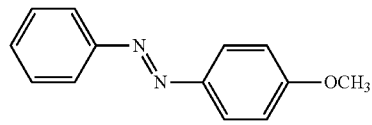

[2]

The modulable absorption compound 300 can also be an indazole, allylated azobenzene with various spacer links, or another version of phenyl azopyrazoles, as shown [3]-[6]:

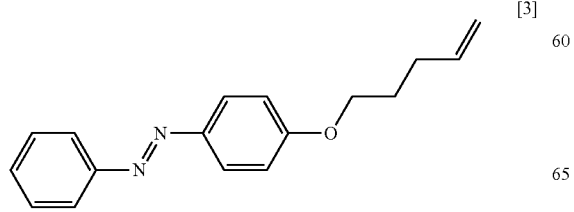

[3]

-continued

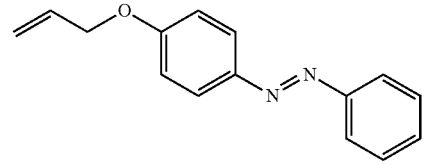

[4]

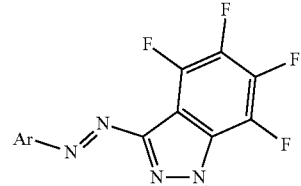

[5]

5-pyrazoles

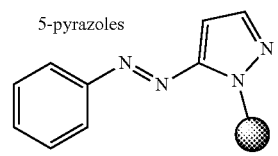

[6]

5 pzH

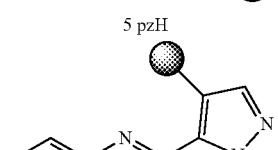

5 pzMe

Figure 9:
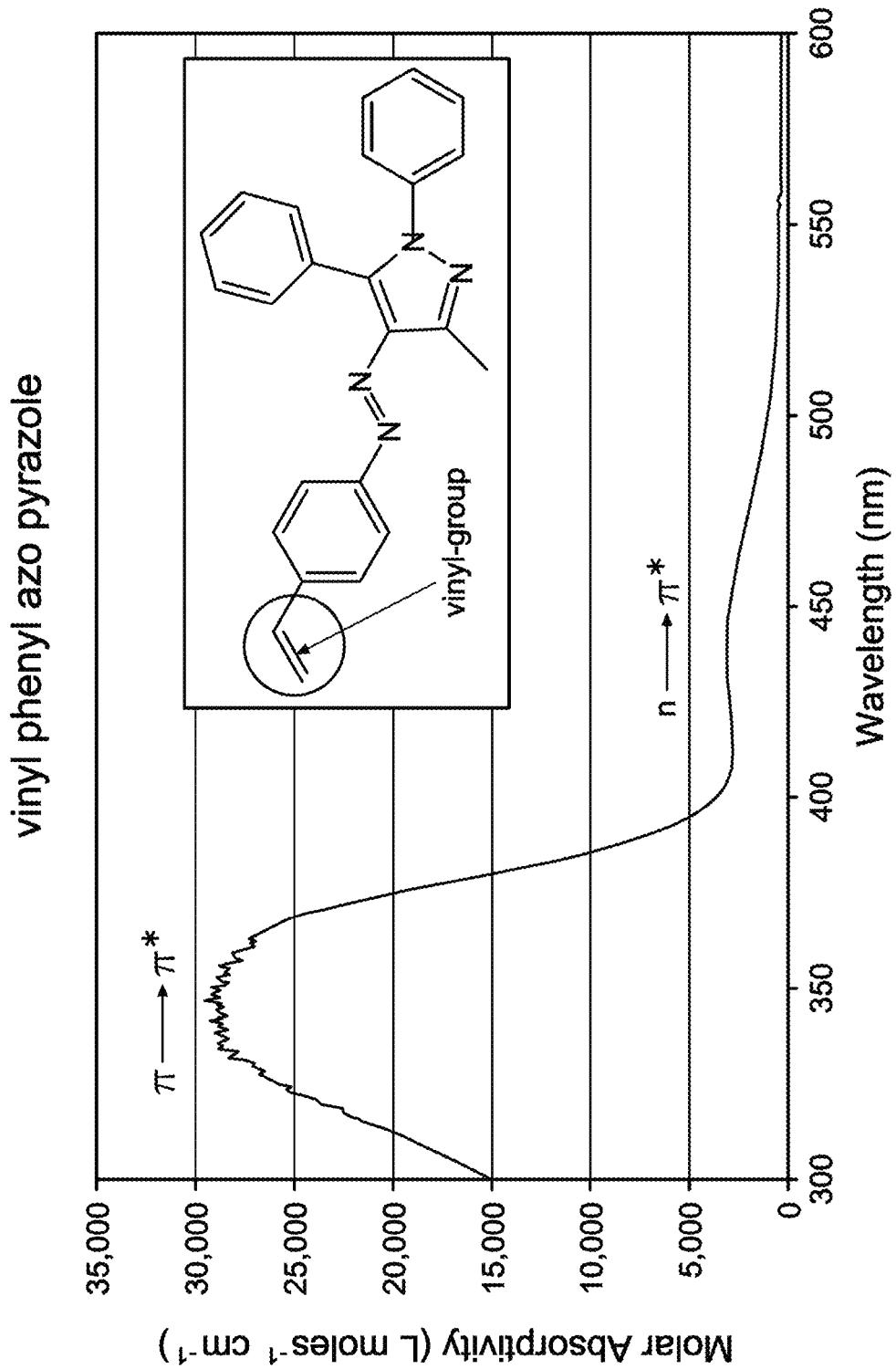
FIG. 9 illustrates the chemical composition and absorption spectrum of the trans photoisomer of vinyl phenyl azo-pyrazole.

FIG. 9 illustrates that in yet other embodiments, the azo-pyrazole can be a vinyl phenyl azo-pyrazole ("VPAP") [7], with the shown absorptivity.

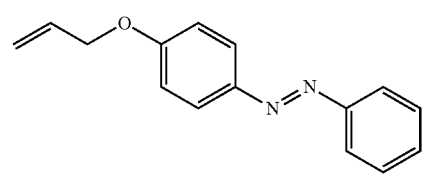

[7]

Finally, in some embodiments, the ethene-aromatic compound can be stilbene [8]:

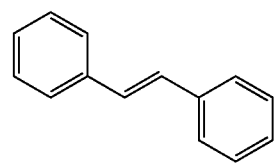

[8]

Figure 10A:
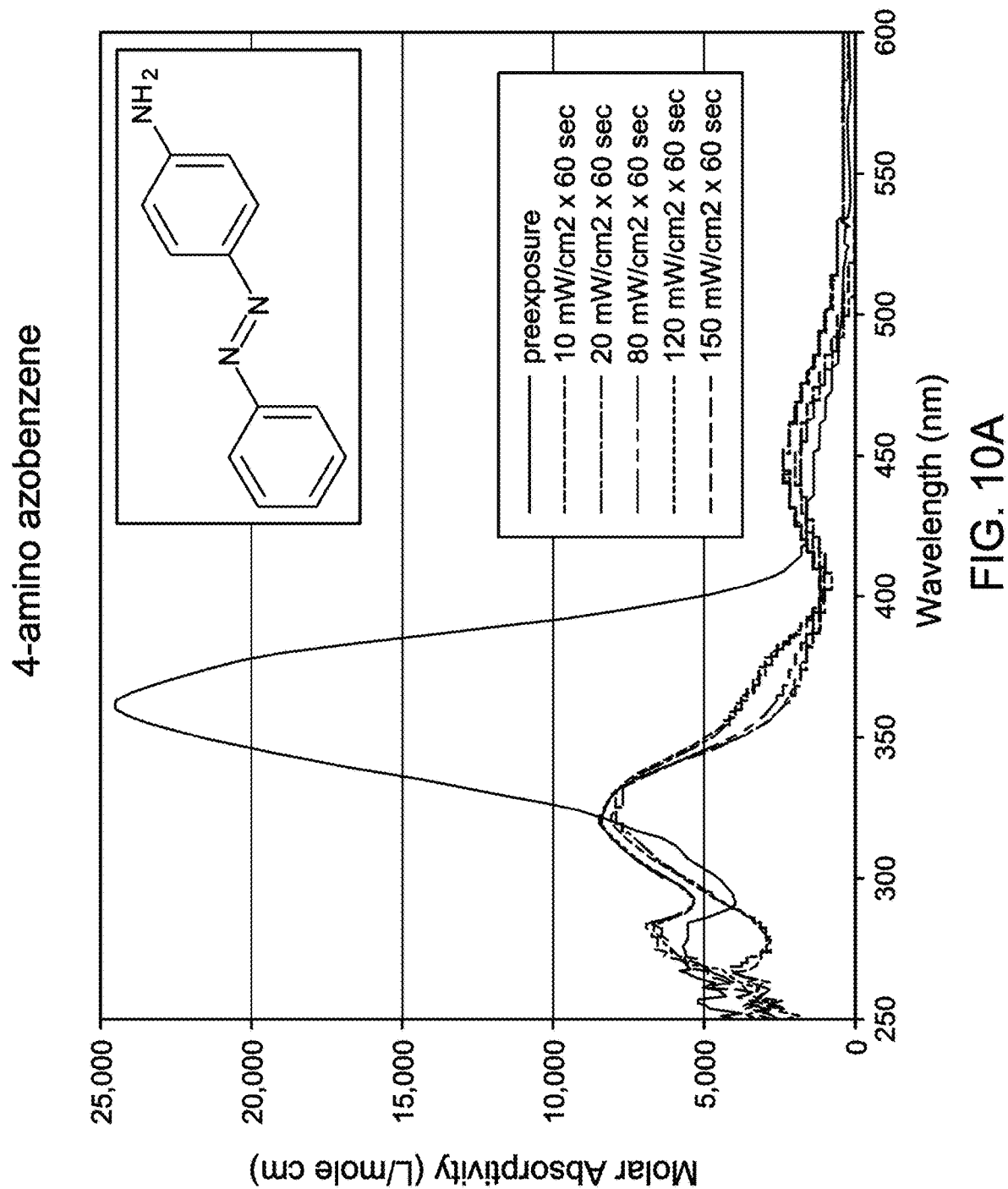
FIG. 10A illustrates the chemical composition and absorption spectrum of 4-amino azobenzene.
Figure 10B:
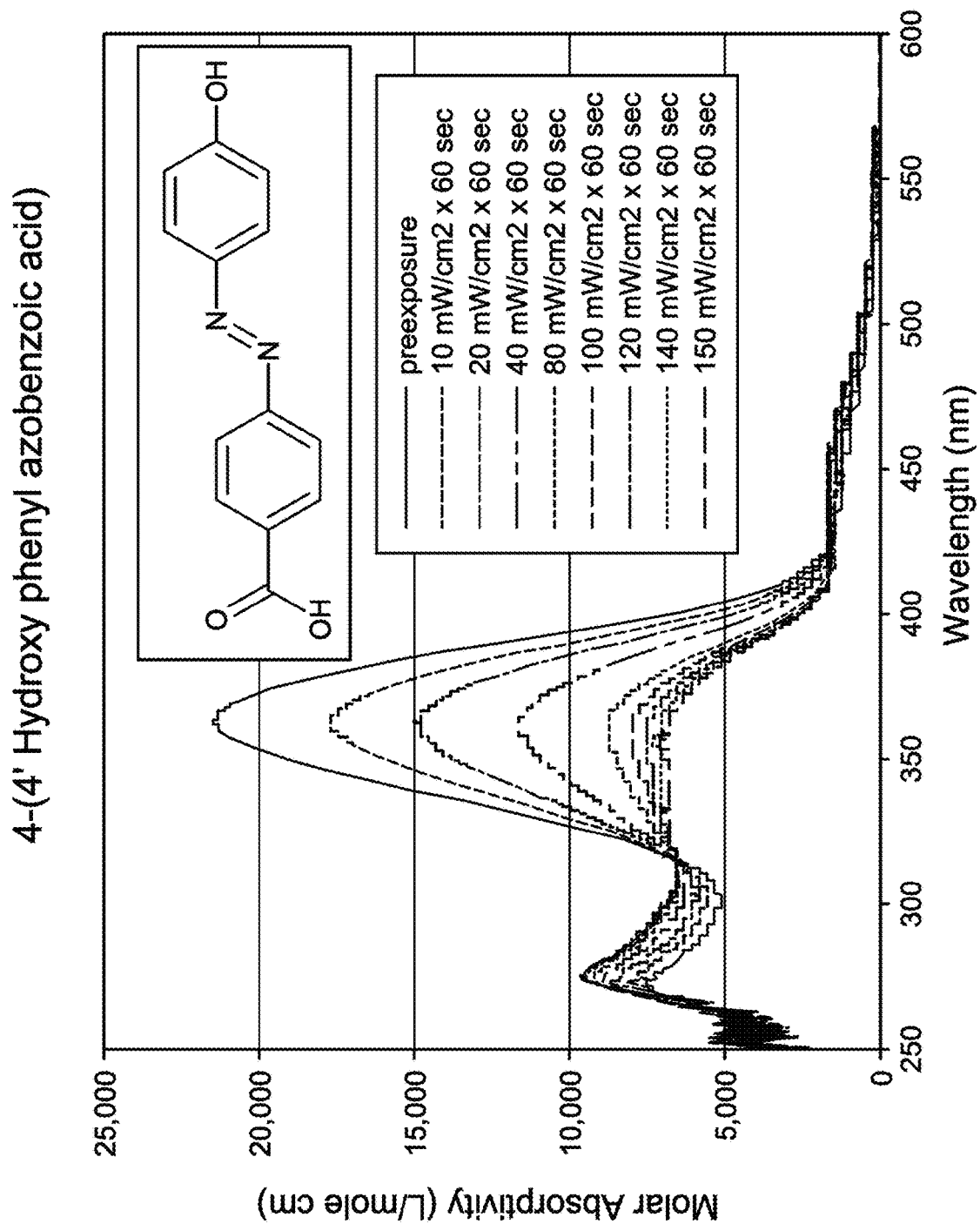
FIG. 10B illustrates the chemical composition and absorption spectrum of 4-(4' hydroxy phenyl azobenzoic acid).

FIGS. 10A-B illustrate a further aspect of embodiments of the modulable absorption compound 300. These Figures show the dependence of the absorptivity curves on the power density of the high-to-low modulating stimulus 310-htl for the case of 4-amino azobenzene in FIG. 10A, and 4-(4' hydroxy phenyl azobenzoic acid) in FIG. 10B. Visibly, 4-amino azobenzene transitions from its high-absorption isomer 300-*h* to its low-absorption isomer 300-*l* already in response to a small power density, or irradiance, such as 10 mW/cm$^2$, applied over 60 seconds; while the 4-(4' hydroxy phenyl azobenzoic acid) transitions only in response to a considerably higher power density around 100 mW/cm$^2$, applied over the same 60 seconds by the high-to-low modulating stimulus 310-*htl*. The selection of the specific modulable absorption compound 300 to be used in a specific embodiment of the MALAL 100 shall be based on characterizations like those in FIGS. 10A-B, as well as on the quantities that appeared in the Eqs. (1)-(7) earlier, such as the quantum yields $\varphi_t$ and $\varphi_c$. E.g. some MALALs 100 can be designed so that only power densities much higher than the solar power density of about 3 mW/cm$^2$ (integrated over the 250-500 nm range portion of the solar spectrum) should induce the transformation from the high-absorption isomer 300-*h* to the low-absorption isomer 300-*l*. In some cases, these power densities, or irradiances, can be defined by integrating the spectrum over a narrower wavelength range, such as over the 300-450 nm range.

Figure 11:
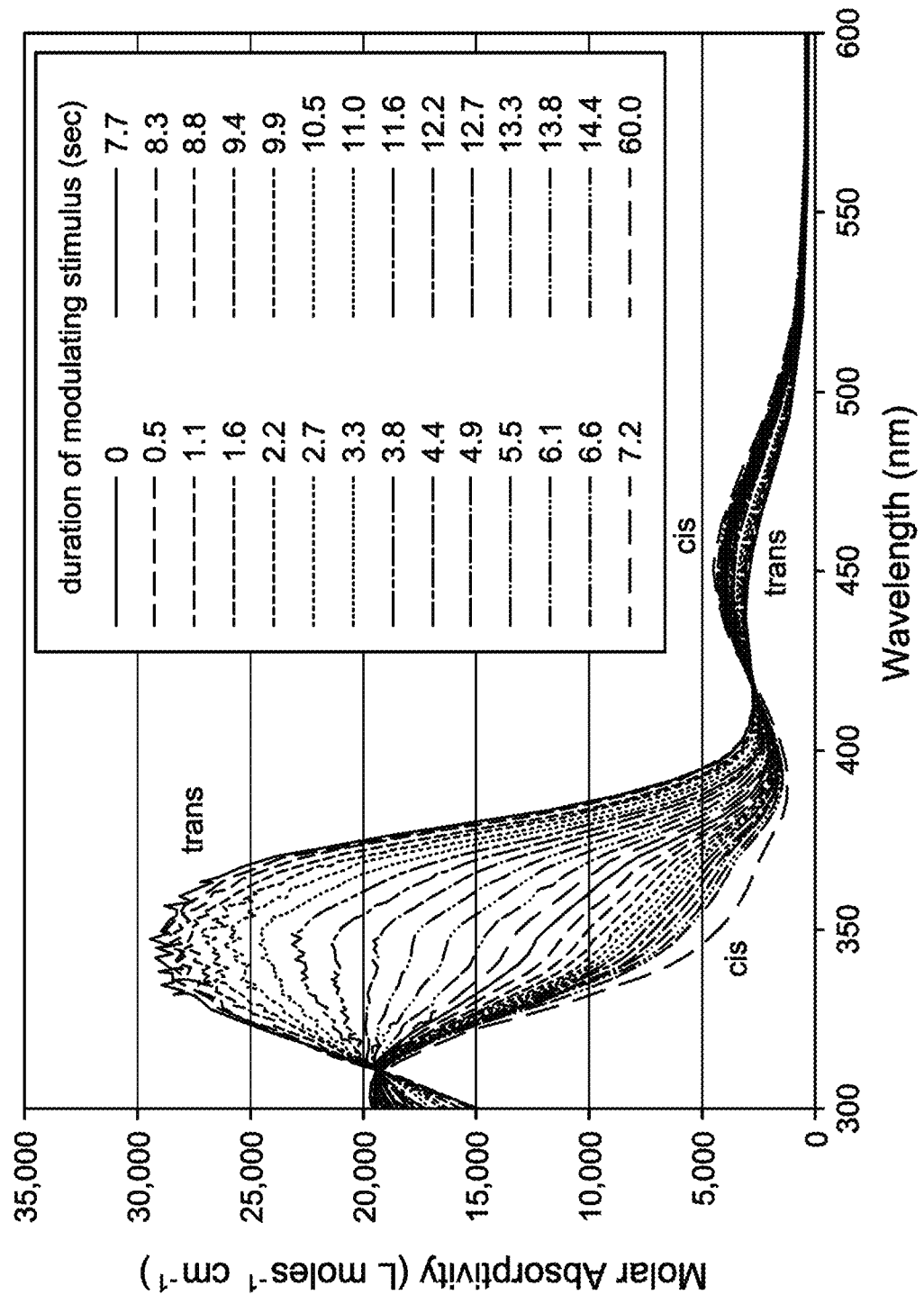
FIG. 11 illustrates the time evolution of the absorptivity during the trans-cis transition.
Figure 12A:
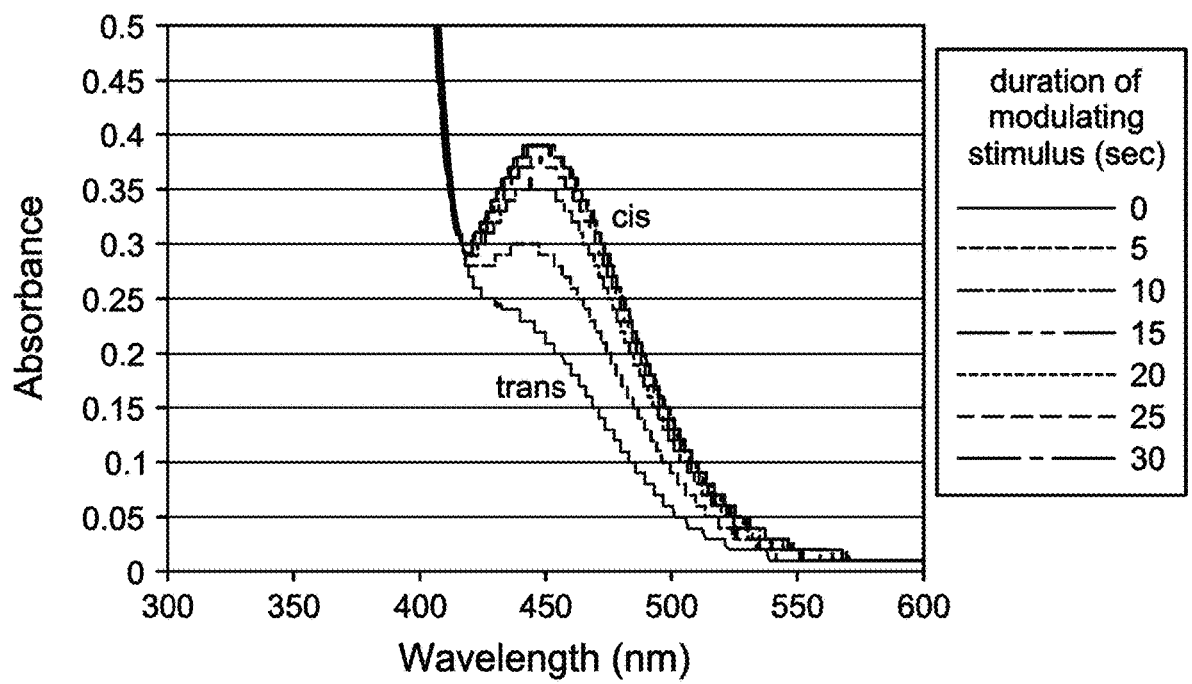
FIGS. 12A-B illustrate the time evolution of the absorptivity during the trans-cis transition, zooming in to the wavelength region in the visible spectrum.
Figure 12B:
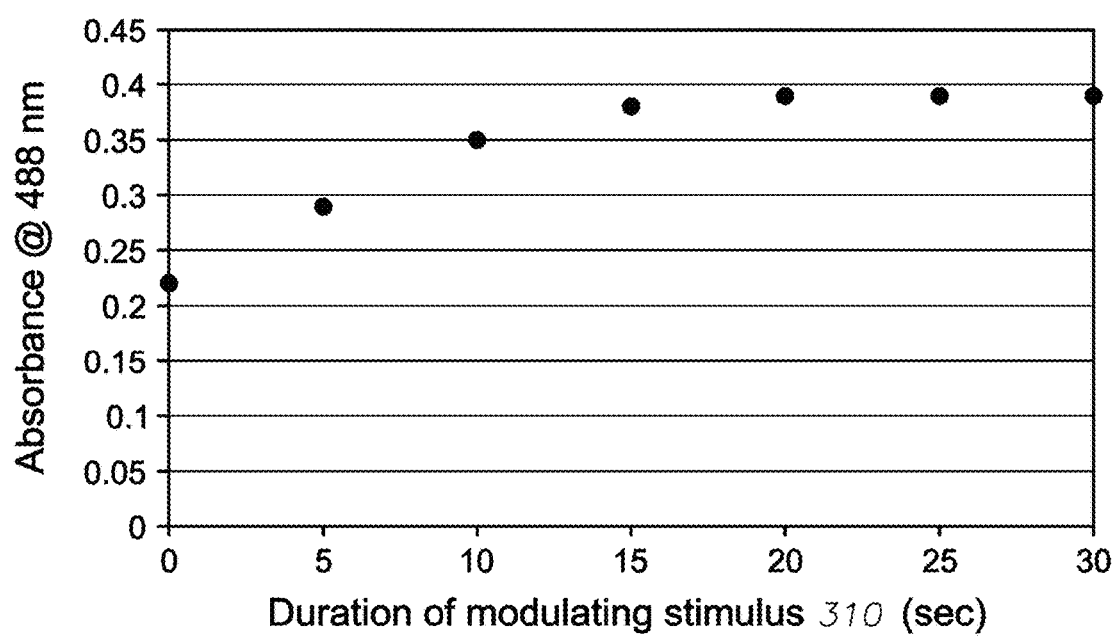

FIGS. 11 and 12A-B illustrate another characteristic of the MALAL 100: the time evolution of the absorptivity as the high-absorption trans isomer 300-*h* transitions, or transforms, into the low-absorption cis isomer 300-*l* for the case of vinyl phenyl azo-pyrazole (VPAP) being the modulable absorption compound 300. In FIG. 11, the absorption curves have been taken at the indicated times, sweeping the duration of the high-to-low modulating stimulus 310-*htl* from 0 sec to 60 sec. As before, different MALAL design principles can lead to preferring modulable absorption compounds 300 with one type of time dependence over another time dependence.

FIG. 12A zooms in on the time dependence of the absorptivity around 450 nm and shows the absorptivity curves for the high-to-low modulating stimulus 310-*htl* being applied for a duration in the range of 0-30 sec. (Note that the quantity shown in FIG. 12 is absorbance that characterizes the absorption across an entire MALAL 100. This absorbance tracks the molar absorptivities shown in FIGS. 9-10 that are typically measured in solution. The absorbance also has a contribution from the UV absorber 116 dispersed in the LAL 110 that introduces a large additional absorbance below a wavelength of about 400 nm.) The UV radiant exposure was kept fixed at 150 mJ/cm$^2$. FIG. 12B plots the time-dependence of the absorptivity, or the related absorbance, at the specific wavelength of 448 nm, as a function of the duration of the modulating stimulus 310. These curves establish that the high-to-low modulating stimulus 310-*htl* is capable of transforming a large fraction of the modulable absorption compound VPAP 300 into its low-absorptivity isomer 300-*l* over a time of about 20 seconds when applied with a UV radiant exposure of 150 mJ/cm$^2$. 20 seconds is a short enough duration to demonstrate that this absorption modulation MALAL technology is compatible with the expectations of expedient light treatments.

For the many other embodiments of the MALAL 100, the high-to-low modulating stimulus 310-*htl* can include a high-to-low illumination with a light having a band centered at a wavelength in a range of 300-400 nm; and the low-to-high modulating stimulus 310-*lth* can include a low-to-high illumination with a light having a band centered at a wavelength in a range of 300-700 nm, including the solar spectrum. In other words, when referencing an illumination and its wavelength, this wavelength often means the illumination having a band with a center peak at the mentioned wavelength, the band also having a bandwidth around this center wavelength, since the source of the illumination in many cases is not a coherent laser, and thus the illumination has a finite bandwidth, or spectral spread. For the high-to-low modulating stimulus 310-*htl* the source can be a narrow band source with a width of the band can be in the 1-50 nm range, in other embodiments in the 1-10 nm range, such as a mercury lamp or a UV LED. For the low-to-high modulating stimulus 310-*lth*, the source can have a quite broad band, including even the regular solar spectrum that extends from about 300 nm beyond 2,500 nm.

As described earlier, for some modulable absorption compounds 300, the naturally occurring thermal relaxation may be already sufficient to play the role of the low-to-high modulating stimulus 310-*lth* by inducing the transition from the low-absorption chromophore 300-*l* to the high-absorption chromophore 300-*h*. For MALALs 100 that transition the low-absorption chromophore 300-*l* into the high-absorption chromophore 300-*h* with thermal relaxation, the description in terms of a light source with a band center peak and a band width is not a natural characterization.

In some embodiments of the MALAL 100, the terms "low absorption" and "high absorption" can be articulated quantitatively. In some MALALs 100, a ratio of an absorptivity of the high-absorption conformation 300-*h* relative to an absorptivity of the low-absorption conformation 300-*l* at a wavelength in a range of 300-400 nm can be greater than 2. As an example, for a 4-amino azobenzene-based modulable absorption compound 300, the ratio of absorptivities is about 5, if a reference wavelength of 350 nm is selected, as shown in FIG. 10A. This absorptivity ratio can be also called a contrast ratio. For some purposes, other wavelength values can be selected, such as a wavelength in the 360-370 nm range. In some of these embodiments, the just described absorptivity ratio can be greater than 3, ins some cases greater than 4.

In many embodiments of the MALAL 100, the high-absorption conformation 300-*h* of the modulable absorption compound 300 has a lower energy than the low-absorption conformation 300-*l*. Therefore, in equilibrium and in ambient conditions, a ratio of a concentration of the high-absorption isomer 300-*h* relative to a concentration of the low-absorption isomer 300-*l* is greater than 2 in at least one of a solid phase, a dilute solution, and in a host matrix-bonded state. In low light conditions, the energies of these high-absorption isomer 300-*h* and low-absorption isomer 300-*l* control the density ratios of these isomers in ambient conditions according to the exponential activation factors of statistical mechanics.

In some MALALs 100, the modulable absorption compound 300 can have a chemical composition such that at least 25%, or 50% of the high-absorption conformation 300-*h* transitions into the low-absorption conformation 300-*l* under the high-to-low illumination 310-*htl* with a radiant exposure in the range of 1 mJ/cm$^2$-1,000 mJ/cm$^2$, integrated over a wavelength range of 300 nm-400 nm.

It is recalled here that the irradiance of an illumination is measured in units of mW/cm$^2$, whereas the radiant exposure is measured in units of mJ/cm$^2$. Broadly speaking, the radiant exposure can be related to the irradiance as: radiant exposure=irradiance*time. However, in some embodiments of the MALAL 100 this relationship can be more complex than a simple product. The amount of absorption modulation in the MALAL 100 for a modulating stimulus 310 that has twice the irradiance, but half the time may be different, in spite of the product of these two factors having remained the same. Such non-linear relations are sometimes referred to as a violation of reciprocity. This violation occurs, for example, in cases when the thermal relaxation rate $R_{thermal}$ in Eq. (2b) is fast, and comparable to the other rates.

The analogous characterization can be applied for the reverse transformation as well. In some MALAL 100 embodiments, the modulable absorption compound 300 can have a chemical composition such that at least 50% of the low-absorption conformation 300-$l$ transitions into the high-absorption conformation 300-$h$ under the low-to-high modulating stimulus 310-$lth$ with a radiant exposure in the range of 1 m/cm$^2$-1,000 mJ/cm$^2$ over a wavelength range of 300 nm-700 nm. In many embodiments, the source of the high-to-low modulating stimulus 310-$htl$ and the source of the adjusting irradiation 210 can be chosen to be the same, shared source, for example a UV source. A typical example can be a mercury arc lamp, or a UV LED, having a spectral peak around 365 nm. In contrast, in most embodiments, the source of the low-to-high modulating stimulus 310-$lth$ is typically operated at longer wavelengths with a much broader spectrum and is thus distinct from the shared source. As mentioned, for relevant classes of MALALs 100 the ambient light of a doctor's office by itself can be an effective source of the low-to-high modulating stimulus 310-$lth$, emitting in a spectrum that can be mostly concentrated in the visible range of 400-700 nm.

Another way to characterize the effect of the modulating stimulus 310 is in terms of the quantum yields $\varphi_t$ and $\varphi_c$, for the trans-to-cis and the cis-to-trans transitions. In such cases, the modulable absorption compound 300 can have a chemical composition such that $\varphi_t$, the quantum yield of the transition from the high-absorption conformation 310-$h$ into the low-absorption conformation 310-$l$ is greater than 1%. For some MALALs 100, this $\varphi_t$ quantum yield can be higher than 5%, in some higher than 10%. The higher the quantum yield, the lower radiant exposure is sufficient to transform the high-absorption conformation 310-$h$ into the low-absorption conformation 310-$l$. Here the quantum yield is defined in the customary manner of quantum yield=number of induced transformations/number of absorbed photons.

The concept of the quantum yield can be used to further characterize the modulable absorption compound 300 as follows. The modulable absorption compound 300 can have a chemical composition such that $\varphi_t$, the quantum yield of the transition from the high-absorption isomer 300-$h$ to the low-absorption isomer 300-$l$ in response to the high-to-low modulating stimulus 310-$htl$ can be in the 1-20% range, while $\varphi_c$, the quantum yield of the reverse transition from the low-absorption isomer 300-$l$ to the high-absorption isomer 300-$h$ in response to the low-to-high modulating stimulus 310-$lth$ can be in the 10-70% range. In other embodiments, these two quantum yields can be in the ranges of $\varphi_t$=5-10%, and $\varphi_c$=40-60%, respectively.

Figure 13:
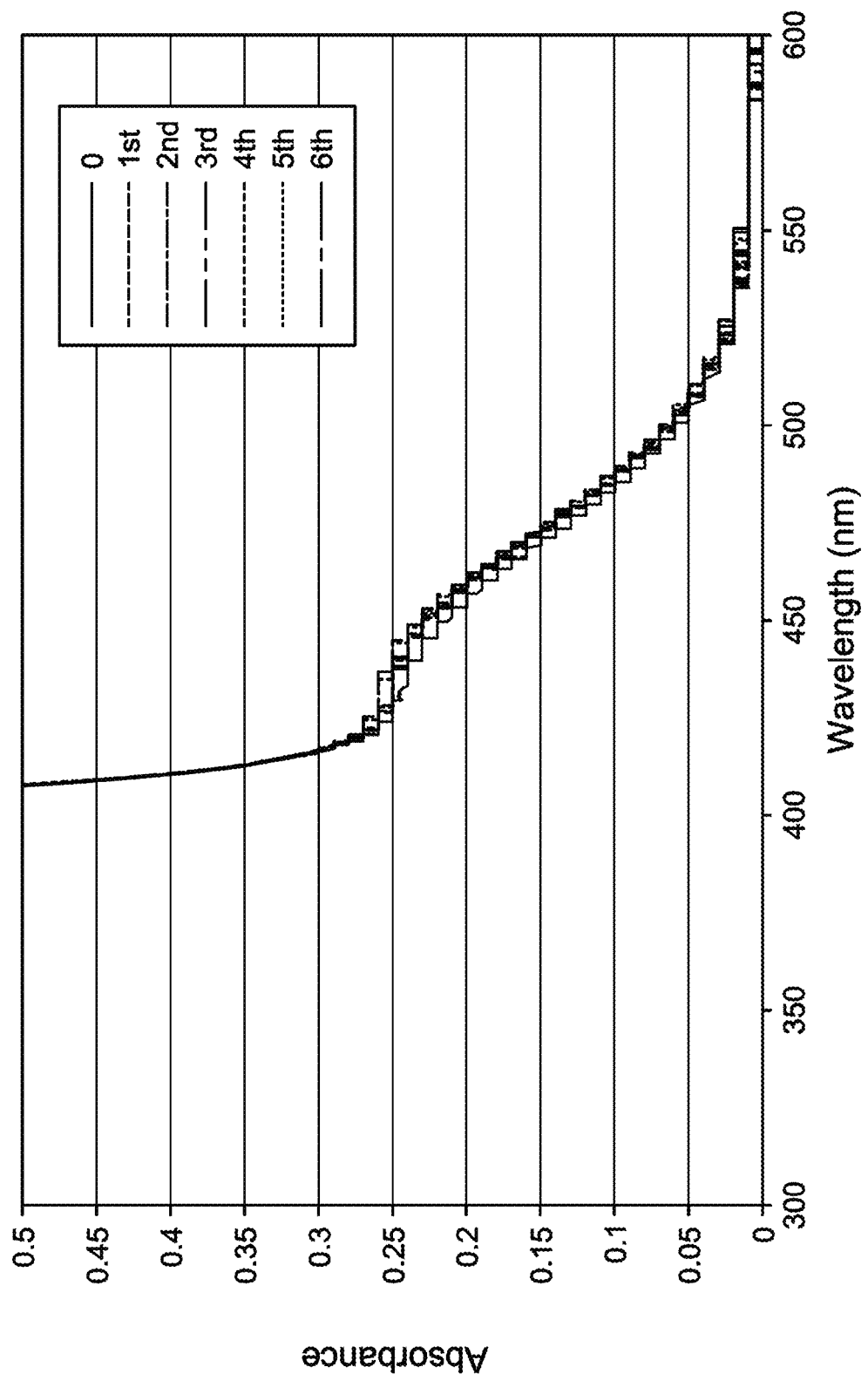
FIG. 13 illustrates the reversibility of absorption modulation.

FIG. 13 illustrates that a couple days after the adjustment procedure ended in FIG. 5D, the increased optical power of the MALAL 100 needs to be locked in by the lock-in irradiation 220, as shown in FIG. 5E. However, the unpolymerized photopolymerizable macromers 113 need to be protected from accidental UV radiation in the time between the ending of the adjusting procedure and the lock-in procedure. To provide this protection, the modulable absorption compound 300 of the front protection layer 120 can be switched back to the high-absorption isomer 300-$h$ at the end of the adjusting irradiation 210 of FIG. 5B, only to be transformed yet again from the high-absorption conformation 300-$h$ to the low-absorption conformation 300-$l$ at the beginning of the lock-in irradiation 220 of FIG. 5E. Clearly, the modulable absorption compound 300 needs to be trans-formable, or switchable, repeatedly upon absorbing the high-to-low modulating stimulus 310-$htl$ and the low-to-high modulating stimulus 310-$lth$. FIG. 13 illustrates the absorbance when the modulable absorption compound 300 is vinyl phenyl azo pyrazole after repeated back-and-forth modulations of the modulable absorption compound 300. The Figure is zoomed in to the cis-to-trans absorption peak around 450 nm. FIG. 13 shows that even after six back-and-forth switchings, the absorption spectra is essentially unchanged, thus demonstrating that at least some embodiments of the modulable absorption compound 300 are suitable for repeated modulations between high and low absorption conformations. Some modulable absorption compounds 300 have been demonstrated to be repeatedly switchable 1,000-1,000,000 times with minimal or unmeasurably small degradation.

In some embodiments, the modulable absorption compound 300 includes a photoisomerizable moiety linked to one or more polymerizable moieties. In some embodiments, the modulable absorption compound 300 is described by the Formula [9]:

$$(Z^1)_{n1}\text{—Y—}(Z^2)_{n2} \qquad [9]$$

where Y is a photoisomerizable moiety (e.g., as described above); n1 and n2 are each independently 0, 1, 2 or 3; and each $Z^1$ and $Z^2$ is independently a polymerizable moiety or a crosslinking moiety that is connected to Y via an optional linker.

In some embodiments, in Formula [9], n1 and n2 are each 1, and $Z^1$ and $Z^2$ are each independently connected to Y via a linker of 1 to 20 atoms in length (e.g., 1 to 6 atoms in length). In some embodiments, n1 is 2 or 3, and each $Z^1$ is attached to Y via a branched linker (e.g., an amino or an ammonium containing linker). In some embodiments, when n1 and/or n2 is 2 or 3, then each $Z^1$ and/or $Z^2$ is independently connected to Y via a linear linker that is not branched. In some embodiments Y is an azoarylene, a diarylethene, or a dithienylethene. In some embodiments, each $Z^1$ and $Z^2$ is independently selected from a vinyl, a vinylidene, a diene, an olefin, an allyl, an acrylate, an acrylamide and an acrylic acid.

In some embodiments, in Formula [9], the modulable absorption compound 300 has the structure Ar$^1$—N=N—Ar$^2$ or Ar$^1$—C=C—Ar$^2$, where Ar$^1$ and Ar$^2$ are independently selected from aromatic 6-membered rings that may be substituted or unsubstituted and may include one or more heteroatoms. In some embodiments, the modulable absorption compound 300 includes an azobenzene moiety (e.g., where Ar$^1$ and Ar$^2$ are phenyl). In some embodiments, the modulable absorption compound 300 is capable of photoisomerization from a trans isomer to a cis isomer, e.g., as exemplified for the Ar$^1$—N=N—Ar$^2$ compound below shown below. In some embodiments, the cis isomer of the modulable absorption compound 300 spontaneously isomerizes back to the trans isomer.

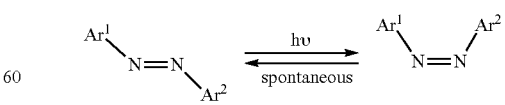

In some embodiments, the azobenzene moiety is a photoisomerizable chromophore having absorption maximum near that of a photoinitiator (such as any of the photoinitiators used and described herein). In some embodiments, the azobenzene moiety has an absorption maximum about 50 nm or less (e.g., about 40 nm or less, about 30 nm or less, about 20 nm or less, or about 10 nm or less) from the absorption maximum of the photoinitiator.

In some embodiments, the thermodynamically more stable trans-azobenzene (t-AB) moiety tends to absorb at lower wavelengths than the corresponding cis-azobenzene (c-AB) isomer. Upon irradiation, photoisomerization may be facile and quantitative. In some embodiments, thermal relaxation from the c-AB moiety to the t-AB isomer occurs within hours (e.g., within 12 hours or less, such as 6, 5, 4, 3, 2 or within 1 hour or less) at ambient temperature. Irradiation of the t-AB moiety near its absorption maximum causes isomerization to the cis isomer and a change in the absorption spectrum (e.g., a shift in the absorption maxima).

In some embodiments, the modulable absorption compound 300 further includes a polymerizable moiety, i.e., a functional group capable of polymerization in a prepolymer composition upon application of a suitable stimulus (e.g., activation of a photoinitiator). The polymerizable moiety may include a functional group such as an alkenyl, a vinyl, a vinylidene, a diene, an olefin, an allyl, an acrylate or a (meth)acrylic functional group. In some embodiments, the polymerizable moiety is an allyl or a vinyl group.

In some embodiments, where the modulable absorption compound 300 comprises a polymerizable moiety, the modulable absorption compound 300 may be chemically incorporated into another component of the compositions of interest. For example, the modulable absorption compound 300 can be incorporated into the backbone of a polymer that is present as a matrix material (see below). Also, for example, the modulable absorption compound 300 can be incorporated into the backbone or as a sidegroup of the prepolymer (see below). In this way, small molecule modulable absorption compound 300s can be chemically incorporated into polymeric components of the compositions of interest. In some embodiments and for some applications, incorporating modulable absorption compound 300s in this manner makes it less likely for the masking component to diffuse out of the compositions of interest.

In some embodiments, the modulable absorption compound 300 is described by the structure of Formula [10]:

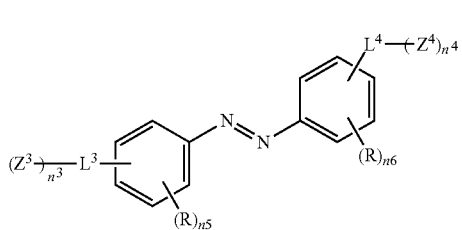

[10]

where:

$n^3$ and $n^4$ are each independently 0, 1, 2 or 3;

$(Z^3)_{n3}$-$L^3$- and -$L^4$-$(Z^4)_{n4}$ may be independently absent or present;

each $Z^3$ and $Z^4$ is independently a polymerizable moiety or a crosslinking moiety;

$L^3$ and $L^4$ are linkers;

$n^3$ and $n^6$ are each independently 0, 1, 2, 3, 4 or 5, provided that when $(Z^3)_{n3}$-$L^3$- is present, $n^5$ is not 5, and when -$L^4$-$(Z^4)_{n4}$ is present, $n^6$ is not 5; and each R is independently selected from the group consisting of hydrogen, a hydrocarbyl (e.g., alkyl, alkenyl, aryl, etc.), a heterocycle, a halogen, a haloalkyl or perhaloalkyl (e.g., trifluoromethyl), an amino, hydroxyl, an ether, nitro, cyano, carboxy, an acyl, an amido, an ester, a thiol, a thioether, a sulfonyl and a sulfonamide.

In some embodiments, in Formula [10], each $Z^3$ and $Z^4$ is independently selected from a vinyl, a vinylidene, a diene, an olefin, an allyl, an acrylate, an acrylamide and an acrylic acid.

In some embodiments, in Formula [10], $L^3$ and $L^4$ are each independently a linker of 1 to 20 atoms in length, such as of 1 to 6 atoms in length. In some embodiments, the linker $L^3$ and/or $L^4$, when present, may include an amino group that connects to a polymerizable moiety or a crosslinking moiety. In some embodiments, a linker is present and includes a branched amino group (e.g., a trivalent amino or a tetravalent ammonium group) for connecting two or three polymerizable moieties and/or crosslinking moieties to the azobenzene. In some embodiments, $L^3$ and/or $L^4$ is a branched amino (—N=) group. In some embodiments, $L^3$ and/or $L^4$ is a branched ammonium (—N(+)=) group. In some embodiments, $L^3$ includes a branched amino or ammonium group, $n^3$ is 2 or 3, and $Z^3$ is an allyl or a vinyl.

In some embodiments, in Formula [10], $L^3$ and $L^4$, when present, may be attached to the azobenzene ring at any convenient positions. For example, $L^3$ may be attached to the first phenyl ring at the 2, 3 or 4 position relative to the azo substituent. For example, $L^4$ may be attached to the second phenyl ring at the 2', 3' or 4' position relative to the azo substituent. All combinations of $L^3$ and/or $L^4$ positioning around the first and second phenyl rings, respectively, are envisaged. For example, $L^3$ and $L^4$ may be attached at the 2 and 2' positions, respectively. For example, $L^3$ and $L^4$ may be attached at the 3 and 3' positions, respectively. For example, $L^3$ and $L^4$ may be attached at the 4 and 4' positions (i.e., para), respectively. Alternatively, $L^3$ may be attached at the 4-position of the first phenyl ring, and $L^4$ may be attached at the 2' position of the second phenyl ring. Exemplary arrangements of $L^3$ and $L^4$ are shown in the compounds described below.

In some embodiments, the modulable absorption compound 300 is described by the structure of Formula [11]:

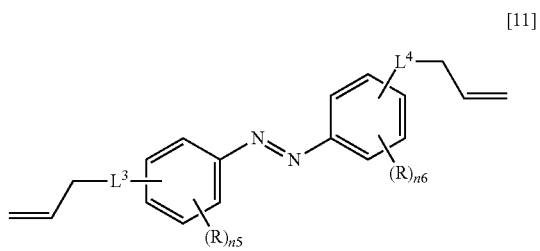

[11]

where $L^3$ and $L^4$ are linkers;

$n^5$ and $n^6$ are each independently 0, 1, 2, 3 or 4; and each R is independently selected from the group consisting of hydrogen, a hydrocarbyl (e.g., alkyl, alkenyl, aryl, etc.), a heterocycle, a halogen, a haloalkyl or perhaloalkyl (e.g., trifluoromethyl), an amino, hydroxyl, an ether, nitro, cyano, carboxy, an acyl, an amido, an ester, a thiol, a thioether, a sulfonyl and a sulfonamide.

In some embodiments, the modulable absorption compound 300 is as described by [11] except that one or both of the terminal allyl groups may be independently replaced with any convenient polymerizable moiety or crosslinking moiety, as described herein.

In some embodiments, in Formula [11], one or both of $L^3$ and $L^4$ are connected to the azobenzene via an electron withdrawing substituent, such as, a carbonyl, an ester, an amido, a sulfonyl or a sulfonamide. In some embodiments $L^3$ and $L^4$ are independently —$(CH_2)_{m1}$—$Z^4$—$(CH_2)_{m2}$— where $m^1$ and $m^2$ are each independently 0 or an integer from 1 to 6, and $Z^4$ is selected from a carbonyl (—C(=O)—), an ester (—C(=O)O—), an amido (e.g., —C(=O)NH—), a carbamate (e.g., —OC(=O)NH—), a sulfonyl (—$SO_2$—), a sulfonamide (e.g., —$SO_2$NH—), an ether (—O—), a thioether (—S—) or a urea group (e.g., —NHC(=NH)NH—). In some embodiments, $m^1$ is 2 and $m^2$ is 0. In some embodiments, $Z^4$ is —O—.

In some embodiments, the modulable absorption compound 300 is described by one of the following Formulae [12]-[14]:

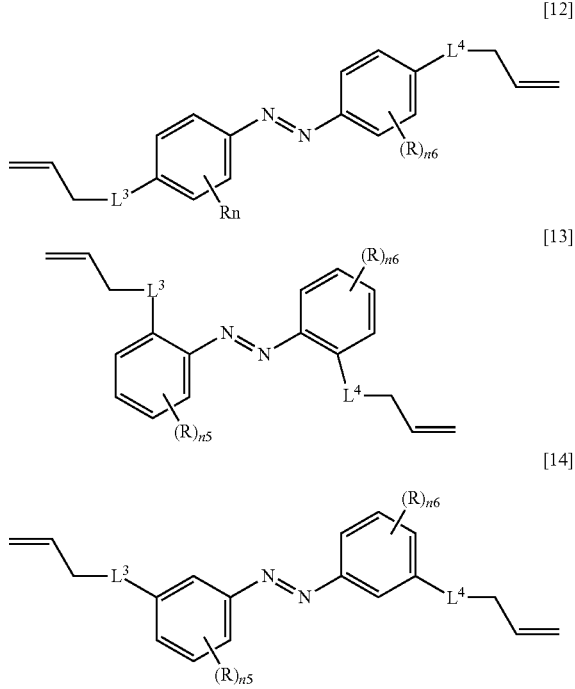

[12]

[13]

[14]

where $L^3$, $L^4$, $(R)_{n5}$ and $(R)_{n6}$ are defined above for Formula [11]. In certain embodiments, $L^3$ and $L^4$ are independently selected from —O— and —O$(CH_2)_m$— where m is an integer from 1 to 6, (e.g., m is 2). In some embodiments, each R is hydrogen.

In some embodiments, the modulable absorption compound 300 is described by the structure of Formulae [15] or [16]:

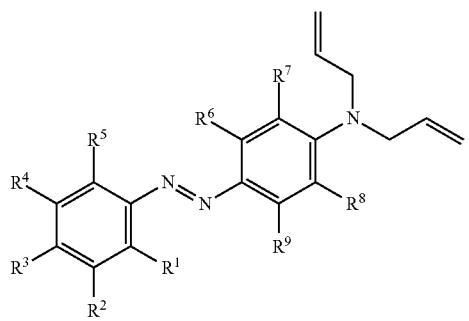

[15]

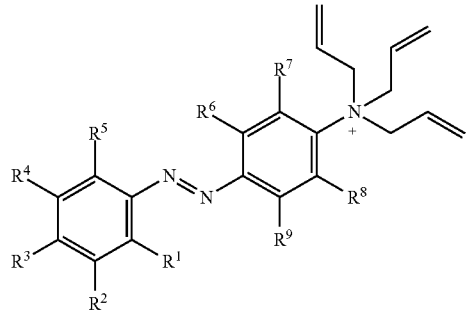

[16]

where $R^1$-$R^8$ are each independently selected from the group consisting of hydrogen, a hydrocarbyl (e.g., alkyl, alkenyl, aryl, etc.), a heterocycle, a halogen, a haloalkyl or perhaloalkyl (e.g., trifluoromethyl), an amino, hydroxyl, an ether, nitro, cyano, carboxy, an acyl, an amido, an ester, a thiol, a thioether, a sulfonyl and a sulfonamide.

In some embodiments, in Formulae [15] or [16], one or more of $R^1$-$R^8$ is -$L^5$-O—$CH_2CH=CH_2$, where $L^5$ is an optional linker group. In some embodiments, in Formulae [15] or [16], each $L^5$ is a $C_1$-$C_6$ alkyl chain (e.g., a $C_2$ alkyl). In some embodiments, in Formulae [15] or [16], each $L^5$ is absent. In some embodiments, in Formulae [15] or [16], $R^1$-$R^8$ are each hydrogen.

In some embodiments, the modulable absorption compound 300 is described by the structure of Formula [17]:

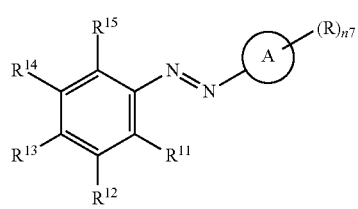

[17]

where A is a heterocycle ring;
$n^7$ is 0 or an integer from 1 to 5;
each R is independently selected from the group consisting of hydrogen, -$L^5$-$(Z^5)_m$ where m is 1, 2 or 3, a hydrocarbyl (e.g., alkyl, alkenyl, aryl, etc.), a heterocycle, a halogen, a haloalkyl or perhaloalkyl (e.g., trifluoromethyl), an amino, hydroxyl, an ether, nitro, cyano, carboxy, an acyl, an amido, an ester, a thiol, a thioether, a sulfonyl and a sulfonamide;
$R^{11}$-$R^{15}$ are each independently selected from the group consisting of hydrogen, a hydrocarbyl (e.g., alkyl, alkenyl, aryl, etc.), a heterocycle, a halogen, a haloalkyl or perhaloalkyl (e.g., trifluoromethyl), an amino, hydroxyl, an ether, nitro, cyano, carboxy, an acyl, an amido, an ester, a thiol, a thioether, a sulfonyl and a sulfonamidea hydrocarbyl (e.g., alkyl, alkenyl, aryl, etc.), a heterocycle, a halogen, a haloalkyl or perhaloalkyl (e.g., trifluoromethyl), an amino, hydroxyl, an ether, nitro, cyano, carboxy, an acyl, an amido, an ester, a thiol, a thioether, a sulfonyl and a sulfonamide, and -$L^5$-$Z^5$; and
$L^5$ is a linker and each $Z^5$ is independently a polymerizable group or a crosslinking group.

In some embodiments, in Formula [17], A is a N-linked heterocycle, such as but not limited to, morpholino, thiomorpholino piperidino, piperazino, homopiperazine, azepano, or pyrrolidino. In some embodiments, in Formula [17], A is a N-linked heterocycle (e.g., an Nmorpholino or a N-piperidinyl).

In some embodiments, the modulable absorption compound 300 is described by the structure of Formula [18]:

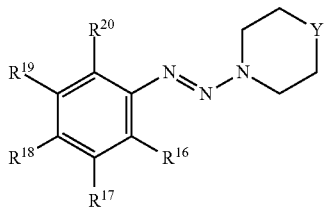

[18]

where Y is O or N—$R^{21}$, where $R^{21}$ is hydrogen, an alkyl, an aryl, an acyl, a heterocycle, or -$L^3$-$Z^3$;

$R^{16}$-$R^{20}$ are each independently selected from the group consisting of hydrogen, a hydrocarbyl (e.g., alkyl, alkenyl, aryl, etc.), a heterocycle, a halogen, a haloalkyl or perhaloalkyl (e.g., trifluoromethyl), an amino, hydroxyl, an ether, nitro, cyano, carboxy, an acyl, an amido, an ester, a thiol, a thioether, a sulfonyl and a sulfonamide, and -$L^5$-$Z^5$; and $L^5$ is a linker and $Z^5$ is a polymerizable group or a crosslinking group.

In some embodiments, in Formula [18], each L is independently a $C_1$-$C_6$ alkyl chain (e.g., a $C_2$ alkyl).

In some embodiments, in Formula [18], at least one (e.g., two) of $R^{16}$-$R^{20}$ and $R^{21}$ includes a polymerizable moiety (e.g., an allyl group) or a crosslinking moiety. In some embodiments, in Formula [18], at least one of $R^{16}$-$R^{20}$ and $R^{21}$ includes an allyl or a vinyl group. In some embodiments, in Formula [18], $R^{18}$ is —$(CH_2)_{m1}$-$L^6$-$(CH_2)_{m2}$—$Z^6$ where $m^1$ and $m^2$ are each independently 0 or an integer from 1 to 6, and $L^6$ is selected from a carbonyl (—C(=O)—), an ester (—C(=O)O—), an amido (e.g., —C(=O)NH—), a carbamate (e.g., —OC(=O)NH—), a sulfonyl (—$SO_2$—), a sulfonamide (e.g., —$SO_2$NH—), an ether (—O—), a thioether (—S—) or a urea group (e.g., —NHC(=NH)NH—). In some embodiments, $m^1$ is 2 and $m^2$ is 0. In some embodiments, $L^6$ is —O—.

In some embodiments, at least one of $R^6$-$R^{20}$ and $R^{21}$ (e.g., $R^{18}$, $R^{19}$ or $R^{20}$) is -$L^7$-O—$CH_2CH=CH_2$, where $L^7$ is an optional linker group, possibly a $C_1$-$C_6$ alkyl chain (e.g., a $C_2$ alkyl).

In some embodiments, in Formula [18], Y is O. In some embodiments, in Formula [18], one or more of $R^{16}$-$R^{20}$ is nitro. In some embodiments, in Formula [18], $R^{18}$ is nitro, and $R^{16}$, $R^{17}$, $R^{19}$ and $R^{20}$ are hydrogen.

In some embodiments, the modulable absorption compound 300 is selected from one of the following Formulae [19]-[25]:

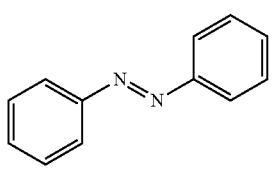

[19]

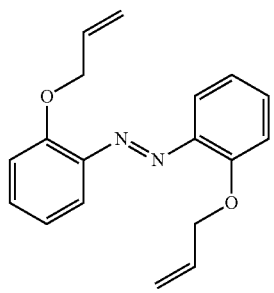

[20]

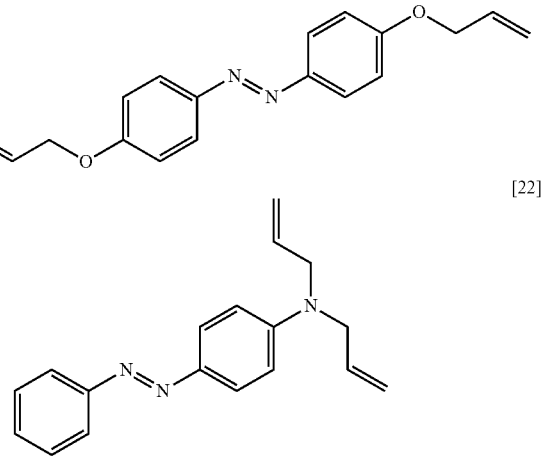

[21]

[22]

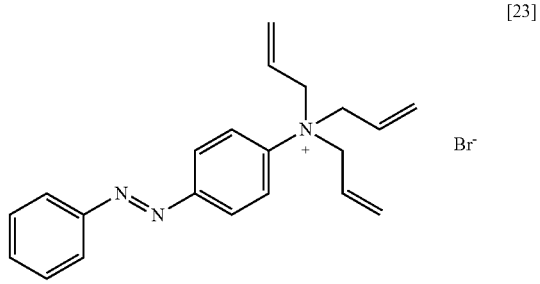

[23]

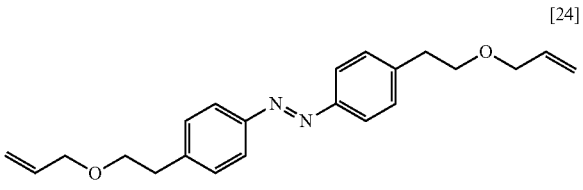

[24]

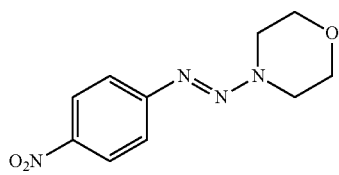

[25]

To avoid unwanted photoinitiated polymerization or crosslinking induced by ambient sunlight during healing, the modulable absorption compound 300 is included in the front protection layer 120 to block such photoinitiation by absorbing the UV component of the incident light. The photoinitiator 115 and the modulable absorption compound 300 can be selected to have overlapping absorption spectra, so that the modulable absorption compound 300 is capable of absorbing sufficient ambient UV to prevent the activation of the photoinitiator 115. Upon application of the high-to-low modulating stimulus 310-*htl*, photoisomerization of the modulable absorption compound in its high-absorptivity isomer 300-*h* results in a shift in the absorption maximum of the modulable absorption compound 300 away from that of the photoinitiator 115, such that the absorption spectra overlap of the photoisomerized modulable absorption compound 300 and the photoinitiator 115 is substantially reduced at a wavelength suitable for activation of the photoionitiator 115.

In some embodiments, photoisomerization of the modulable absorption compound 300 occurs via a cis-trans isomerization, a cyclization reaction, or a ring-opening reaction. Convenient photoisomerizable compounds include compounds that are capable of blocking absorption by the photoinitiator 115 and that experience a significant shift in absorption maxima upon application of a suitable modifying stimulus 310. In some embodiments, the modulable absorption compound 300 undergoes a cyclization or ring-opening photoisomerization upon absorption of the modifying stimulus 310.

In some embodiments, the modulable absorption compound 300 includes a photoisomerizable moiety that is a stilbene (e.g., an azastilbene), an azobenzene moiety, an azoarylene, a fulgide, a spiropyran, a naphthopyran, a quinone, a spirooxazine, a nitrone, a triaryl methane (e.g., a triphenyl methane), a thioindigo, a diarylethene, a dithienylethene, or an overcrowded alkene. In some embodiments, the modulable absorption compound 300 includes an alkenyl (C=C) or an azo moiety (—N=N—) moiety that undergoes photoisomerization via a cis-trans transition. In some embodiments, the modulable absorption compound 300 includes a diarylethene that undergoes photoisomerization via an electrocyclic cyclization reaction. In some embodiments, the modulable absorption compound 300 includes a spiropyran that undergoes photoisomerization via a ring opening transition.

In some embodiments, the photoisomerizable moiety is selected from an azoarylene, a diarylethene, and a dithienylethene.

In some embodiments, photoisomerization of the modulable absorption compound 300 results in a second isomer that is thermally unstable, e.g., the second isomer will revert to the first isomer when the light source is removed. In such cases, photoisomerization is reversible.

In some MALALs 100, the modulable absorption front protection layer 120 can further include an additional non-modulable ultraviolet-absorbing compound having a chemical composition, absorptivity and thickness sufficient to prevent an adjustment of the optical properties of the light adjustable lens when exposed to a radiant exposure up to 10,000 mJ/cm$^2$ integrated over a wavelength range of 300 nm-400 nm, at irradiances not exceeding 3 mW/cm$^2$. In some embodiments, the radiant exposure can be up to 50,000 mJ/cm$^2$.

Figure 14A:
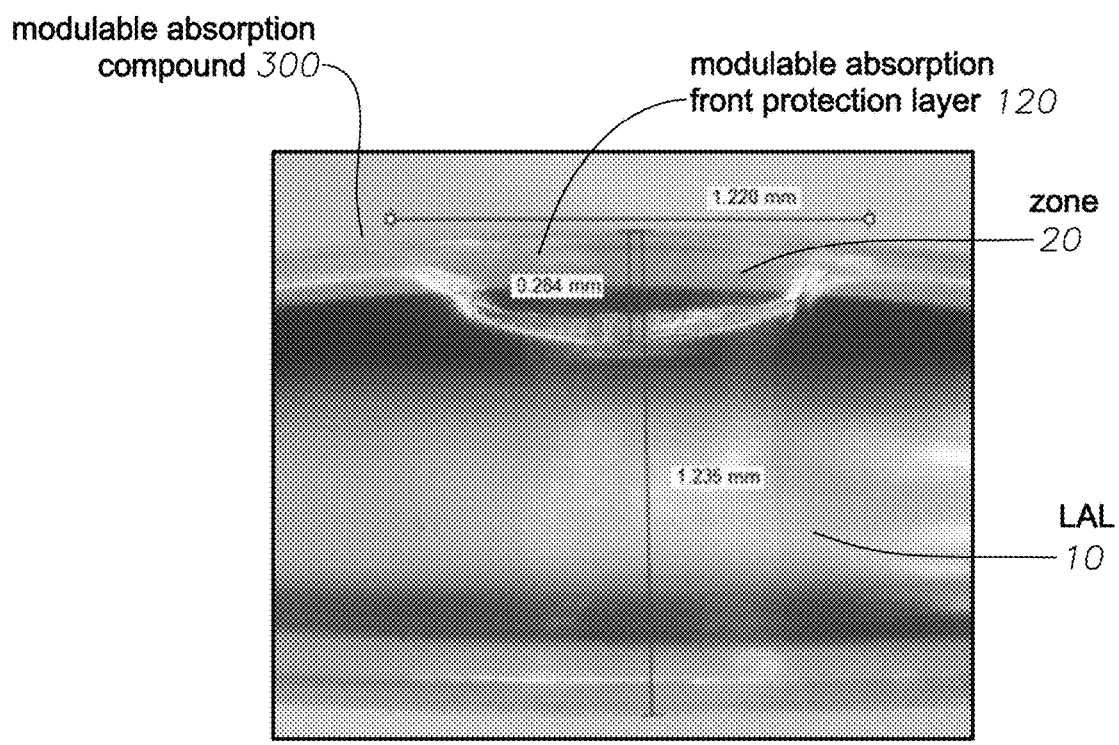
FIGS. 14A-C illustrate a possible but very unlikely formation of small zones in MALALs 100.
Figures 14B, 14C:
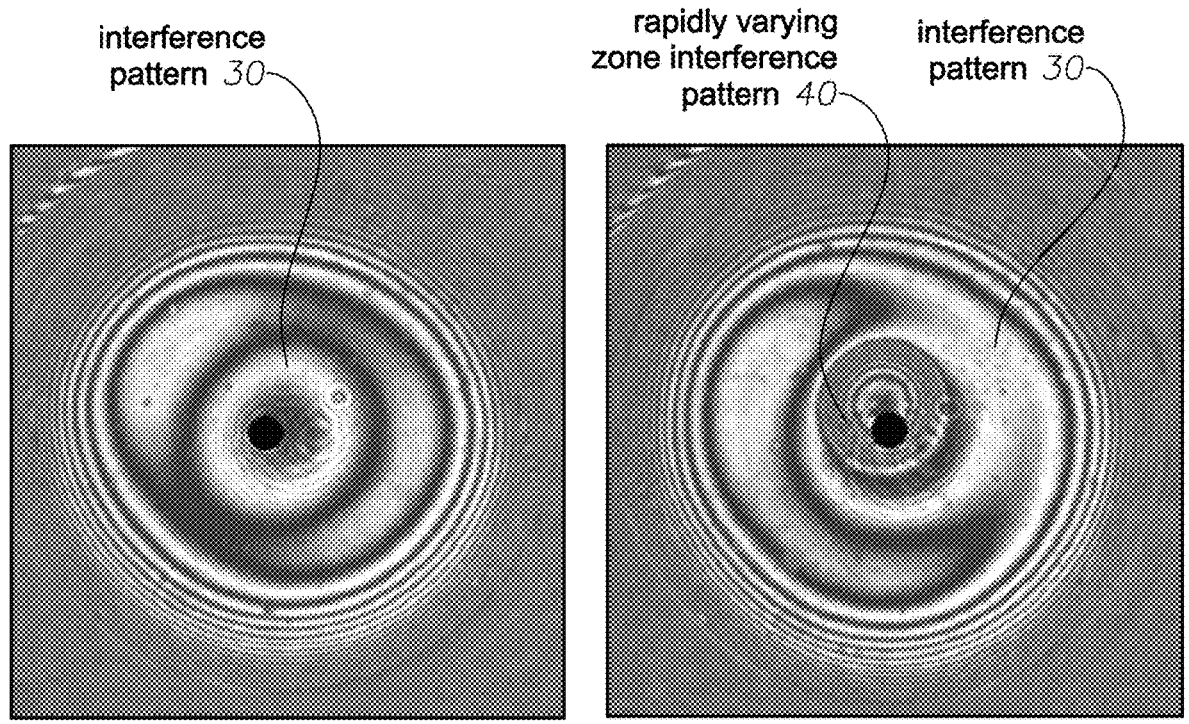

FIGS. 14A-C illustrate one more attractive aspect of the here-described MALAL 100 embodiments. Because of the presence of the modulable absorption front protection layer 120, even in the very unlikely case of exposure to an excessive amount of UV irradiation, only a small fraction of the incident UV irradiation is capable of getting past the front protection layer 120. Therefore, even if a zone 20 is formed in such an unlikely case, its size is considerably smaller than the zones that form in LALs that have no such front protection layer 120, as shown e.g. in FIGS. 2A-B. FIG. 14A shows the formed unusually small zone 20 within a cross section of the MALAL 100, and FIGS. 14B-C show the formation of a small zone 20 as detected via a rapidly varying interference pattern 40 appearing in a standard interferometry.

If the size of the accidental zone 20 is so small, then it is possible to perform additional measurements before the adjustment step of FIG. 5B, and to modify the spatial profile of the adjusting irradiation 210 such that the combined effect of the accidental zone 20 and the modified adjusting irradiation 210 together induce the planned adjustment of the optical properties of the LAL 110. In other embodiments, the adjusting irradiation 210 can be applied with a spatial profile that simply approximately compensates the optical effect of the small zone 20. The same can be implemented if the accidental zone 20 was formed after the adjustment step of FIG. 5B but before the lock-in step of FIG. 5E, in which case the profile of the lock-in irradiation 220 is to be adjusted to compensate the presence of the accidental zone 20.

The protective ability of the front protection layer 120 can be captured in yet another manner: in some embodiments of the MALAL 100, an absorption-modulation time $T_{am}$ of the front protection layer 120 can be shorter than a zone-formation time $T_{zf}$ of the light adjustable lens 110: $T_{am} = < T_{zf}$. In some representative cases, the absorption-modulation time (the time it takes for the modulable absorption compound 300 to transition from the low-absorptivity isomer 300-*l* to the high absorptivity isomer 300-*h*) can be in the 0.1 sec-10 sec range, in some others in the 0.1 sec-1 sec range, whereas the zone-formation time of the LAL 110 can be in the 5 sec-100 sec ranges, in some others in the 10 sec-50 sec range. Such front protection layers 120 can efficiently prevent a zone formation even in the very unlikely case of the modulable absorption compound 300 unintentionally getting transitioned from its high-absorption isomer 300-*h* to its low-absorption isomer 300-*l*: the front protection layer 120 can self-heal before the formation of a zone.

Figures 15A, 15B:
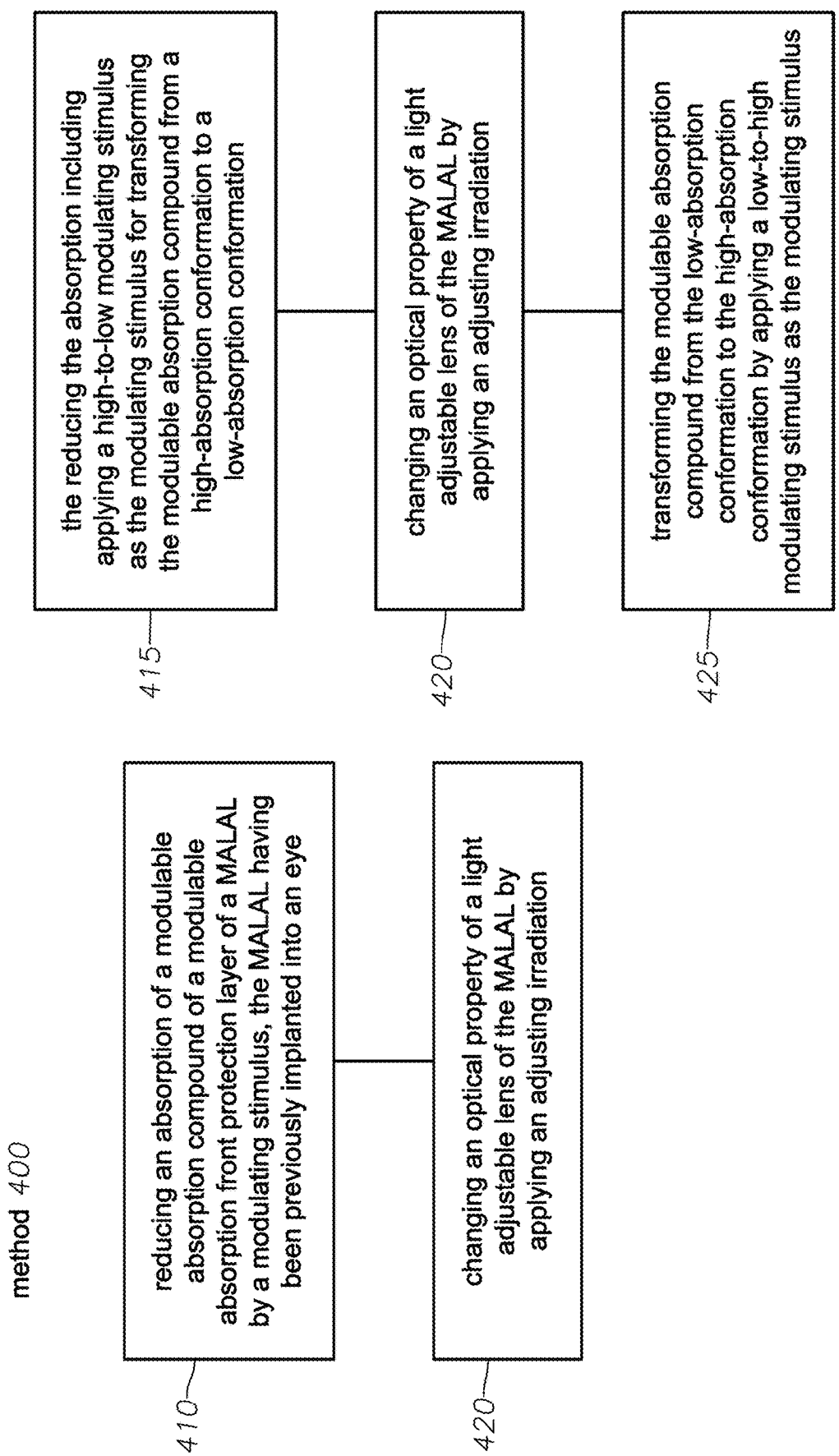
FIGS. 15A-B illustrate steps of a method of adjusting an optical property of a modulable absorption light adjustable lens.

Finally, FIGS. 15A-B illustrate a method 400 of adjusting an optical property of a modulable absorption light adjustable lens MALAL 100, the method comprising the steps of:
  reducing 410 an absorption of a modulable absorption compound 300 of a modulable absorption front protection layer 120 of the MALAL 100 by a modulating stimulus 310, the MALAL 100 having been previously implanted into an eye; and
  changing 420 an optical property of a light adjustable lens of the MALAL 100 by applying an adjusting irradiation 210.

In some embodiments of the method 400, the reducing 410 the absorption includes applying 415 a high-to-low modulating stimulus 310-*htl* as the modulating stimulus for transforming the modulable absorption compound 300 from a high-absorption conformation 300-*h* to a low-absorption conformation 300-*l*; and the changing 420 of the optical property is followed by transforming 425 the modulable absorption compound 300 from the low-absorption conformation 300-*l* to the high-absorption conformation 300-*h* by applying a low-to-high modulating stimulus 310-*lth* as the modulating stimulus 310. In some cases, the high-to-low modulating stimulus 310-*htl* includes a high-to-low illumination with a light having a narrow band centered at a wavelength in a range of 300-400 nm; and the low-to-high modulating stimulus 310-*lth* includes one of a low-to-high illumination with a light having a broad band centered at a wavelength in a range of 300-700 nm, an ambient illumination, and a thermal relaxation.

While this document contains many specifics, details and numerical ranges, these should not be construed as limitations of the scope of the invention and of the claims, but, rather, as descriptions of features specific to particular embodiments of the invention. Certain features that are described in this document in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to another sub-combination or a variation of a sub-combinations.

The invention claimed is:

1. A modulable absorption light adjustable lens (MALAL) for implantation into an eye, comprising:
   a light adjustable lens that is capable of changing its optical properties upon an adjusting irradiation, including a photo-modifiable material that includes
      a polymer host matrix;
      at least one of monomers and macromere, capable of photo-induced polymerization;
      a photoinitiator; and
      dispersed ultraviolet absorbers;
   a modulable absorption front protection layer, including a modulable absorption compound, dispersed in a frontal region of the light adjustable lens and localized to the polymer host matrix in the frontal region of the light adjustable lens by one or more bonds to a cross-linker of the polymer host matrix, wherein the modulable absorption compound is capable of transforming
      from a high-absorption conformation to a low-absorption conformation upon absorbing a high-to-low modulating stimulus, and
      from the low-absorption conformation to the high-absorption conformation upon absorbing a low to-high modulating stimulus; and
   haptics, extending from the light adjustable lens.

2. The MALAL of claim 1,
   wherein: the polymer host matrix is selected from the group consisting of
   a silicone-based matrix, an acrylate-based matrix, a collamer, a hybrid silicone-acrylate-based matrix, and a multi-layer matrix combining at least two of the preceding matrices.

3. The MALAL of claim 1, wherein:
   the high-to-low modulating stimulus and the low-to-high modulating stimulus each is selected from the group consisting of
   an electromagnetic illumination, an ambient light illumination, a laser irradiation, an infrared irradiation, an ultra-violet illumination, a magnetic stimulus, an electric field, a chemical or thermal stimulus, a heat transfer, an energy transfer, an ultrasound-mediated stimulus, a mechanical stimulus, a thermal stimulus and a thermal relaxation.

4. The MALAL of claim 1 wherein:
   the one or more bonds localizing the modulable absorption compound includes a bond coupling one of a carbon and a silicon to one selected from a group consisting of a carbon, a silicon, an oxygen, a nitrogen, a hydrogen, a sulfur and a halogen atom.

5. The MALAL of claim 1, wherein:
   the modulable absorption front protection layer includes one of
      a layer in the frontal region of the light adjustable lens;
      a layer attached onto the frontal region of the light adjustable lens; and
      a layer deposited onto the frontal region of the light adjustable lens.

6. The MALAL of claim 1, wherein:
   a thickness of the modulable absorption front protection layer is less than 50%, of a thickness of the light adjustable lens.

7. The MALAL of claim 1, wherein:
   the modulable absorption compound is selected from the group consisting of
   an azo-aromatic compound, a diazene, an azo-pyrazole, a dienylethene, a fulgicide, an azulene, a spiropyran, an ethene-aromatic compound, a macromer of one of these compounds, a polymer of these compounds, a composition containing one of these compounds, a composition containing one of these compounds as side-chains, a composition containing one of these compounds as a backbone having a side-chain, and a nanoparticulate bonded to one of these compounds.

8. The MALAL of claim 7, wherein:
   the azo-aromatic compound is one of azobenzene and 4-methoxy azobenzene, the azo-pyrazole is a vinyl phenyl azo-pyrazole, and the ethene-aromatic compound is stilbene.

9. The MALAL of claim 1, wherein:
   the modulable absorption compound is selected from the group consisting of
   a photoswitchable compound, a photoactivatable compound, a photoisomerizable compound, a photochromic compound, a photoconvertible compound, and a switching chromophore.

10. The MALAL of claim 1, wherein:
    the high-to-low modulating stimulus includes a high-to-low illumination with a light having a band centered at a wavelength in a range of 300-400 nm; and
    the low-to-high modulating stimulus includes one of a low-to-high illumination with a light having a band centered at a wavelength in a range of 400-700 nm, an ambient illumination, and a thermal relaxation.

11. The MALAL of claim 10, wherein:
    a ratio of an absorptivity of the high-absorption conformation relative to an absorptivity of the low-absorption conformation at a wavelength in a range of 300-400 nm is greater than 2.

12. The MALAL of claim 10, wherein:
    the high-absorption conformation of the modulable absorption compound has a lower energy than the low-absorption conformation such that
    in equilibrium in ambient conditions, a ratio of a concentration of the modulable absorption compound in the high-absorption conformation relative to a concentration of the modulable absorption compound in the low-absorption conformation is greater than 2 in at least one of a solid phase, a dilute solution, and in a host matrix-bonded state.

13. The MALAL of claim 10, wherein:
    the modulable absorption compound has a chemical composition such that at least 25% of the high-absorption conformation transitions into the low-absorption conformation under the high-to-low illumination with a radiant exposure in the range of 1 $mJ/cm^2$-1,000 $mJ/cm^2$ over a wavelength range of 300 nm-400 nm.

14. The MALAL of claim 13, wherein:
    the modulable absorption compound has a chemical composition such that a quantum yield of a transition from the high-absorption conformation into the low-absorption conformation is greater than 0.01.

15. The MALAL of claim 10, wherein:
the modulable absorption compound has a chemical composition such that at least 50% of the low-absorption conformation transitions into the high-absorption conformation under the low-to-high modulating stimulus with a radiant exposure in the range of 1 $mJ/cm^2$-1,000 $mJ/cm^2$ over a wavelength range of 400 nm-600 nm.

16. The MALAL of claim 1, wherein:
the modulable absorption compound is capable of transforming from the high-absorption conformation to the low-absorption conformation and back to the high-absorption conformation repeatedly upon absorbing the high-to-low modulating stimulus and the low-to-high modulating stimulus, respectively.

17. The MALAL of claim 1, wherein:
the modulable absorption front protection layer further includes an additional non-modulable ultraviolet-absorbing compound having a chemical composition, absorptivity and thickness sufficient to prevent an adjustment of the optical properties of the light adjustable lens when exposed to a radiant exposure up to 10,000 $mJ/cm^2$ integrated over a wavelength range of 300 nm-400 nm, at intensities not exceeding 3 $mW/cm^2$.

* * * * *